US012611200B2

(12) United States Patent
Sato et al.

(10) Patent No.: US 12,611,200 B2
(45) Date of Patent: Apr. 28, 2026

(54) EXCREMENT ANALYSIS APPARATUS, ANALYSIS SYSTEM, SERVER APPARATUS, ANALYSIS METHOD, AND NON-TRANSITORY COMPUTER-READABLE MEDIUM

(71) Applicant: PARAMOUNT BED CO., LTD., Tokyo (JP)

(72) Inventors: Tomoyuki Sato, Kanagawa (JP); Tsutomu Mieno, Kanagawa (JP); Haruhiko Yamabuchi, Kanagawa (JP); Masahiro Wakabayashi, Kanagawa (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 252 days.

(21) Appl. No.: 18/007,601

(22) PCT Filed: May 26, 2021

(86) PCT No.: PCT/JP2021/019943
§ 371 (c)(1),
(2) Date: Dec. 1, 2022

(87) PCT Pub. No.: WO2021/246256
PCT Pub. Date: Dec. 9, 2021

(65) Prior Publication Data
US 2023/0225714 A1 Jul. 20, 2023

(30) Foreign Application Priority Data

Jun. 4, 2020 (JP) ................................ 2020-097575
Oct. 27, 2020 (JP) ................................ 2020-179605

(51) Int. Cl.
*G01N 33/483* (2006.01)
*A61B 10/00* (2006.01)
(Continued)

(52) U.S. Cl.
CPC ..... *A61B 10/0038* (2013.01); *G01N 33/4833* (2013.01); *G01N 33/493* (2013.01); *G01N 2021/177* (2013.01)

(58) Field of Classification Search
CPC ........... A61B 10/0038; G01N 33/4833; G01N 33/493; G01N 2021/177; G01N 21/85;
(Continued)

(56) References Cited

U.S. PATENT DOCUMENTS

| 11,604,177 B1 * | 3/2023 | Park ........................ G01N 31/22 |
| 2019/0195802 A1 * | 6/2019 | Attar ..................... G01J 3/2803 |

(Continued)

FOREIGN PATENT DOCUMENTS

| JP | 2007-252805 A | 10/2007 |
| JP | 2007-323528 A | 12/2007 |

(Continued)

OTHER PUBLICATIONS

Communication dated Apr. 4, 2023 issued by the Japanese Intellectual Property Office in counterpart Japanese Application No. 2020-179605.
(Continued)

*Primary Examiner* — Xin Y Zhong
(74) *Attorney, Agent, or Firm* — Wenderoth, Lind & Ponack, L.L.P.

(57) ABSTRACT

An excrement analysis apparatus includes an inputter, a memory, a first analyzer, and a second analyzer. The inputter inputs imaging data captured by an image capture apparatus installed in such a way as to include, in a capturing range, an excretion range of excrement in a toilet bowl of a toilet. The memory temporarily holds the imaging data input by the inputter. The first analyzer analyzes first analysis target data being the imaging data input by the inputter, and outputs notification information to an observer who observes a user (Continued)

of the toilet. The second analyzer analyzes second analysis target data being the imaging data that is input by the inputter and temporarily held by the memory, and outputs detailed information indicating a content of excretion.

23 Claims, 25 Drawing Sheets

(51) Int. Cl.
*G01N 33/493* (2006.01)
*G01N 21/17* (2006.01)

(58) Field of Classification Search
CPC ........ G01N 21/251; G01N 21/84; G06N 3/09;
G06N 3/08; G16H 40/63; G16H 50/20;
G16H 50/80; G16H 30/40; E03D 11/13;
Y02A 90/10; G16Y 20/00
See application file for complete search history.

(56) References Cited

U.S. PATENT DOCUMENTS

| | | | | |
|---|---|---|---|---|
| 2020/0268303 | A1* | 8/2020 | Oliva | A61B 5/202 |
| 2021/0401244 | A1* | 12/2021 | Kawai | A47K 13/24 |
| 2022/0333364 | A1 | 10/2022 | Furuya et al. | |
| 2023/0071883 | A1* | 3/2023 | Kanai | E03D 11/13 |

FOREIGN PATENT DOCUMENTS

| | | | |
|---|---|---|---|
| JP | 2008-054835 | A | 3/2008 |
| JP | 2009-270951 | A | 11/2009 |
| JP | 2017-072410 | A | 4/2017 |
| JP | 2017-137707 | A | 8/2017 |
| JP | 2017-533423 | A | 11/2017 |
| JP | 2018-510334 | A | 4/2018 |
| JP | 2018-126331 | A | 8/2018 |
| JP | 2019-12049 | A | 1/2019 |
| JP | 2019-071896 | A | 5/2019 |
| JP | 2019-074328 | A | 5/2019 |
| JP | 2021-38640 | A | 3/2021 |
| KR | 101368144 | B1 | 2/2014 |
| WO | 2021/024584 | A1 | 2/2021 |

OTHER PUBLICATIONS

International Search Report for PCT Application No. PCT/JP2021/019943, mailed on Jul. 21, 2021.

Okada, Yasuhiro et al., "Development of image acquisition system for automatic excretion processors and classification method for analysis of stool properties of people using them", Research materials of the Institute of Electrical Engineers of Japan, Joint Technical Meeting on Magnetics and Medical/Biological Engineering, Mar. 19, 2020, pp. 117-120.

* cited by examiner

| | REAL TIME ANALYSIS | NON-REAL TIME ANALYSIS | |
|---|---|---|---|
| INPUT | IMAGE | IMAGE<br>REAL TIME ANALYSIS RESULT | |
| TECHNIQUE | Deep Learning | Deep Learning | Image Processing |
| OUTPUT | FOREIGN BODY<br>FECES<br>FECES + URINE<br>URINE<br>URINE DRIPPING<br>BUTTOCKS WASHING<br>MACHINE | FECES CHARACTERISTIC | FECES COLOR<br>FECES AMOUNT<br>URINE COLOR<br>URINE AMOUNT |

Fig. 5

| DETERMINATION TARGET (OUTPUT) | DETERMINATION TIME | INPUT |
|---|---|---|
| FOREIGN BODY | ALWAYS | OPTICAL CAMERA CAPTURING IMAGE |
| FECES, FECES + URINE, URINE, URINE DRIPPING | SITTING~LEAVING | CAPTURING IMAGE AFTER EXECUTION OF PREPROCESSING |
| BUTTOCKS WASHING MACHINE | SITTING~LEAVING | CAPTURING IMAGE AFTER EXECUTION OF PREPROCESSING |

Fig. 6

| DETERMINATION TARGET (OUTPUT) | | BACKGROUND IMAGE SELECTION | INPUT IMAGE SELECTION |
|---|---|---|---|
| FECES CHARACTERISTIC | | IMAGE AFTER SITTING | LAST FECES IMAGE |
| FECES COLOR | | IMAGE AFTER SITTING | LAST FECES IMAGE |
| FECES AMOUNT | ONLY FECES | IMAGE AFTER SITTING | LAST FECES IMAGE |
| | FECES + URINE | LAST URINE IMAGE BEFORE URINE/FECES | LAST URINE/FECES IMAGE |
| URINE COLOR | | IMAGE AFTER SITTING | LAST URINE IMAGE |
| URINE AMOUNT | | NONE | ALL IMAGE DETERMINED TO BE URINE DRIPPING |

Figure 10:
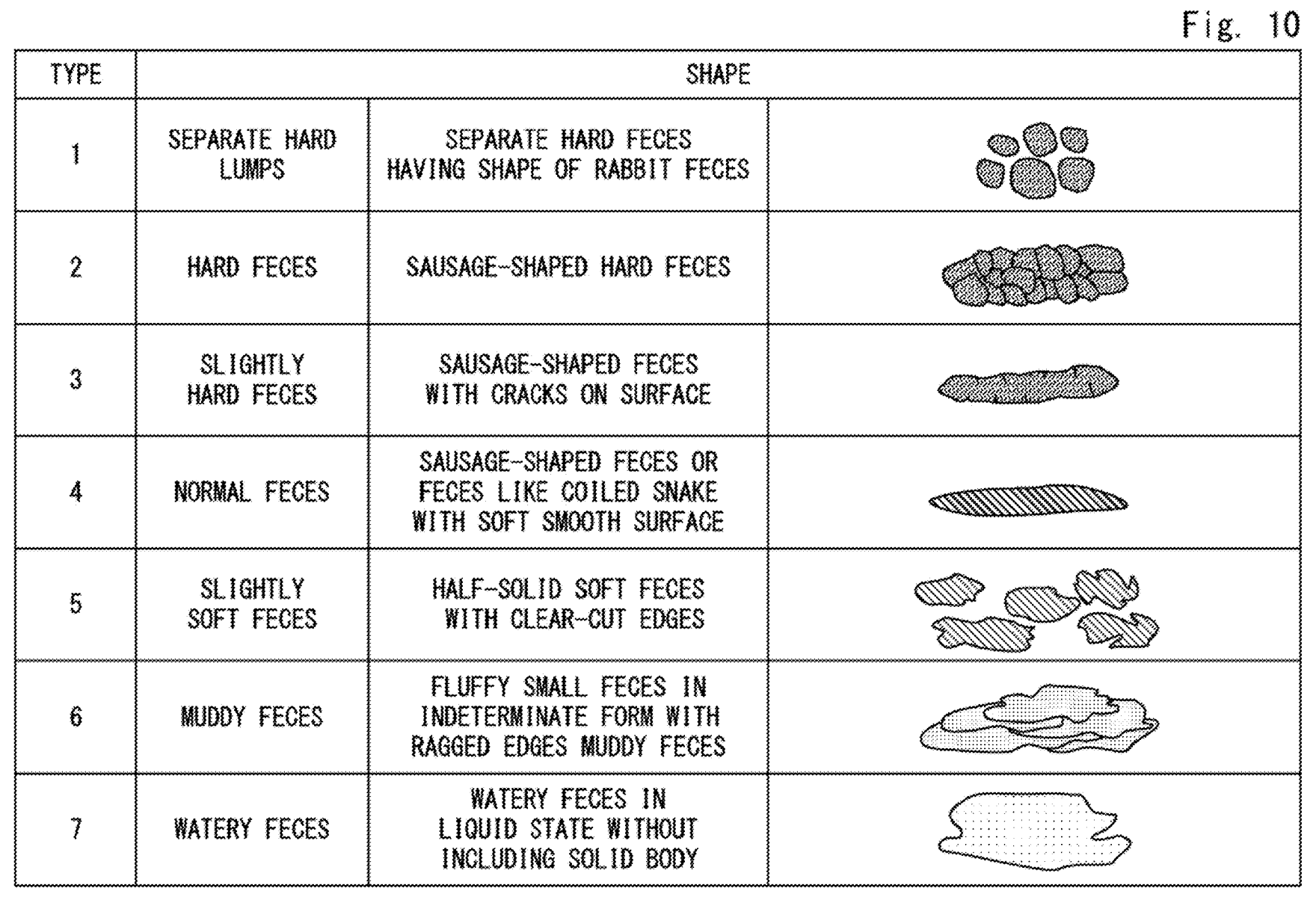

| TYPE | | SHAPE | |
|---|---|---|---|
| 1 | SEPARATE HARD LUMPS | | SEPARATE HARD FECES HAVING SHAPE OF RABBIT FECES |
| 2 | HARD FECES | | SAUSAGE-SHAPED HARD FECES |
| 3 | SLIGHTLY HARD FECES | | SAUSAGE-SHAPED FECES WITH CRACKS ON SURFACE |
| 4 | NORMAL FECES | | SAUSAGE-SHAPED FECES OR FECES LIKE COILED SNAKE WITH SOFT SMOOTH SURFACE |
| 5 | SLIGHTLY SOFT FECES | | HALF-SOLID SOFT FECES WITH CLEAR-CUT EDGES |
| 6 | MUDDY FECES | | FLUFFY SMALL FECES IN INDETERMINATE FORM WITH RAGGED EDGES MUDDY FECES |
| 7 | WATERY FECES | | WATERY FECES IN LIQUID STATE WITHOUT INCLUDING SOLID BODY |

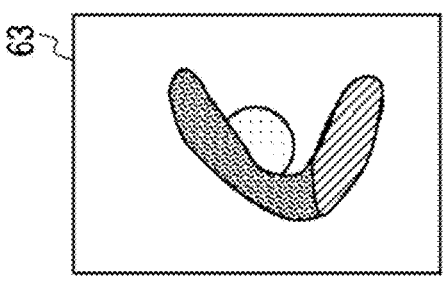
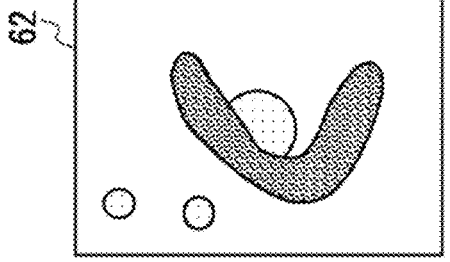
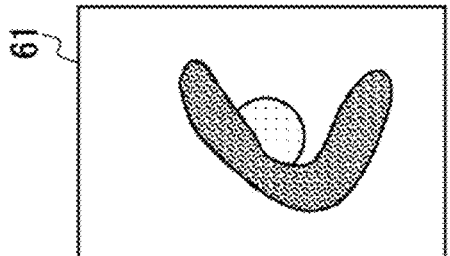
Fig. 11

| CLASS NAME | URINE AMOUNT |
|---|---|
| EXTREMELY SMALL | ~THRESHOLD a |
| SMALL | THRESHOLD a~ THRESHOLD b |
| MEDIUM | THRESHOLD b~ THRESHOLD c |
| GREAT | THRESHOLD c~ THRESHOLD d |
| ESPECIALLY GREAT | THRESHOLD d~ |

Figure 15:
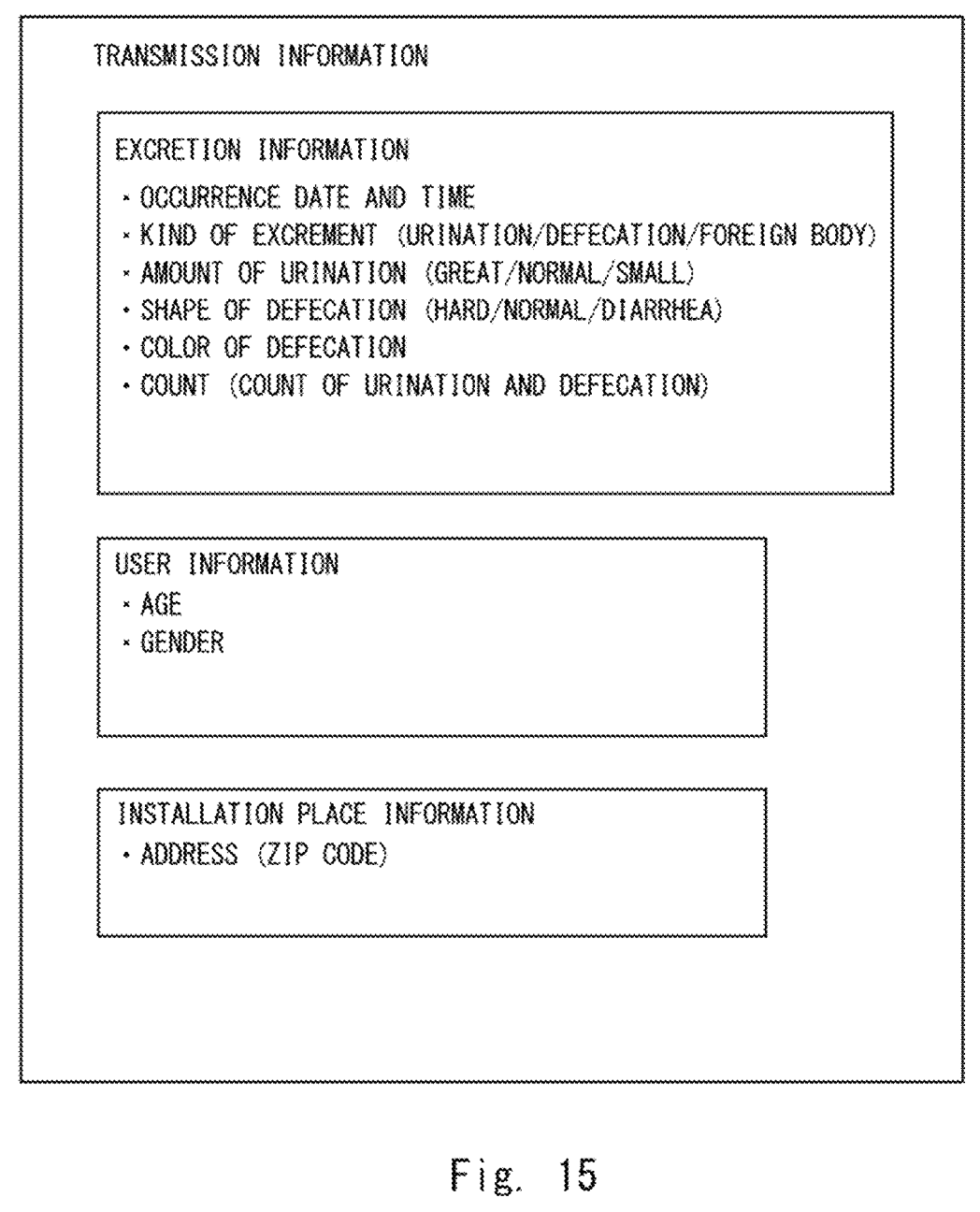

TRANSMISSION INFORMATION

EXCRETION INFORMATION

· OCCURRENCE DATE AND TIME
· KIND OF EXCREMENT (URINATION/DEFECATION/FOREIGN BODY)
· AMOUNT OF URINATION (GREAT/NORMAL/SMALL)
· SHAPE OF DEFECATION (HARD/NORMAL/DIARRHEA)
· COLOR OF DEFECATION
· COUNT (COUNT OF URINATION AND DEFECATION)

USER INFORMATION
· AGE
· GENDER

INSTALLATION PLACE INFORMATION
· ADDRESS (ZIP CODE)

| | OCCURRENCE DATE AND TIME | KIND OF EXCREMENT | AMOUNT OF URINATION | SHAPE OF DEFECATION | COLOR OF DEFECATION | EXCRETION COUNT | AGE | GENDER | ADDRESS (ZIP CODE) |
|---|---|---|---|---|---|---|---|---|---|
| 1 | 2019/7/1 6:24:30 | URINATION | NORMAL | | | 1 | 38 | MALE | 111-1111 |
| 2 | 2019/7/1 6:30:12 | URINATION | NORMAL | | | 1 | 40 | FEMALE | 111-1111 |
| 3 | 2019/7/1 6:35:20 | DEFECATION | | NORMAL | BROWN | 1 | 60 | MALE | 111-2222 |
| 4 | 2019/7/1 7:24:30 | URINATION | GREAT | | | 1 | 22 | MALE | 111-1111 |
| 5 | 2019/7/1 7:41:20 | URINATION | NORMAL | | | 1 | 46 | MALE | 111-1111 |
| 6 | 2019/7/1 8:15:10 | URINATION | NORMAL | | | 1 | 50 | FEMALE | 111-2222 |
| 7 | 2019/7/1 8:24:30 | DEFECATION | | NORMAL | BROWN | 1 | 35 | FEMALE | 111-1111 |
| 8 | 2019/7/1 9:12:56 | URINATION | GREAT | | | 1 | 25 | FEMALE | 111-2222 |
| 9 | 2019/7/1 9:23:34 | URINATION | NORMAL | | | 1 | 60 | FEMALE | 111-1111 |
| 10 | 2019/7/1 9:51:30 | URINATION | SMALL | | | 1 | 80 | MALE | 111-2222 |
| 11 | 2019/7/1 10:11:50 | DEFECATION | | NORMAL | BROWN | 1 | 57 | MALE | 111-1122 |
| 12 | 2019/7/1 10:14:10 | URINATION | NORMAL | | | 1 | 18 | MALE | 111-1111 |
| 13 | 2019/7/1 10:20:30 | URINATION | SMALL | | | 1 | 70 | FEMALE | 111-1122 |

71b

| MONTH | SHAPE OF DEFECATION | | |
|---|---|---|---|
| | HARD | NORMAL | DIARRHEA |
| 1 | | | |
| 2 | | | |
| 3 | | | |
| 4 | | | |
| 5 | | | |
| 6 | | | |
| 7 | | | |
| 8 | | | |
| 9 | | | |
| 10 | | | |
| 11 | | | |
| 12 | | | |

AGE

| MONTH | YOUNGER THAN TEENS | | | TEENS | | | TWENTIES | | | THIRTIES | | | FORTIES | | | FIFTIES | | | SIXTIES | | | SEVENTIES | | | EQUAL TO OR OLDER THAN EIGHTIES | | |
|---|---|---|---|---|---|---|---|---|---|---|---|---|---|---|---|---|---|---|---|---|---|---|---|---|---|---|---|
| | SHAPE OF DEFECATION | | | SHAPE OF DEFECATION | | | SHAPE OF DEFECATION | | | SHAPE OF DEFECATION | | | SHAPE OF DEFECATION | | | SHAPE OF DEFECATION | | | SHAPE OF DEFECATION | | | SHAPE OF DEFECATION | | | SHAPE OF DEFECATION | | |
| | HARD | NORMAL | DIARRHEA | HARD | NORMAL | DIARRHEA | HARD | NORMAL | DIARRHEA | HARD | NORMAL | DIARRHEA | HARD | NORMAL | DIARRHEA | HARD | NORMAL | DIARRHEA | HARD | NORMAL | DIARRHEA | HARD | NORMAL | DIARRHEA | HARD | NORMAL | DIARRHEA |
| 1 | | | | | | | | | | | | | | | | | | | | | | | | | | | |
| 2 | | | | | | | | | | | | | | | | | | | | | | | | | | | |
| 3 | | | | | | | | | | | | | | | | | | | | | | | | | | | |
| 4 | | | | | | | | | | | | | | | | | | | | | | | | | | | |
| 5 | | | | | | | | | | | | | | | | | | | | | | | | | | | |
| 6 | | | | | | | | | | | | | | | | | | | | | | | | | | | |
| 7 | | | | | | | | | | | | | | | | | | | | | | | | | | | |
| 8 | | | | | | | | | | | | | | | | | | | | | | | | | | | |
| 9 | | | | | | | | | | | | | | | | | | | | | | | | | | | |
| 10 | | | | | | | | | | | | | | | | | | | | | | | | | | | |
| 11 | | | | | | | | | | | | | | | | | | | | | | | | | | | |
| 12 | | | | | | | | | | | | | | | | | | | | | | | | | | | |

| MONTH | REGION | | | | | | | | | | | |
|---|---|---|---|---|---|---|---|---|---|---|---|---|
| | 111-1111 | | 111-1112 | | 111-1122 | | 111-2222 | | ⋮ | ⋮ | ⋮ | |
| | SHAPE OF DEFECATION | | SHAPE OF DEFECATION | | SHAPE OF DEFECATION | | SHAPE OF DEFECATION | | | | | |
| | HARD | NORMAL | DIARRHEA | HARD | NORMAL | DIARRHEA | HARD | NORMAL | DIARRHEA | HARD | NORMAL | DIARRHEA |
| 1 | | | | | | | | | | | | |
| 2 | | | | | | | | | | | | |
| 3 | | | | | | | | | | | | |
| 4 | | | | | | | | | | | | |
| 5 | | | | | | | | | | | | |
| 6 | | | | | | | | | | | | |
| 7 | | | | | | | | | | | | |
| 8 | | | | | | | | | | | | |
| 9 | | | | | | | | | | | | |
| 10 | | | | | | | | | | | | |
| 11 | | | | | | | | | | | | |
| 12 | | | | | | | | | | | | |

Fig. 19

START

S41  RECEIVE TRANSMISSION INFORMATION

S42  STORE TRANSMISSION INFORMATION

S43  AGGREGATE TRANSMISSION INFORMATION
     FOR EACH DEFECATION SHAPE

S44  ANALYZE TIME CHANGE IN DEFECATION
     SHAPE FOR EACH REGION

S45  PREDICT SPREAD OF INFECTIOUS DISEASE
     FOR EACH REGION, BASED ON ANALYSIS
     RESULT AND CAUTION INFORMATION

END

71e

| | OCCURRENCE DATE AND TIME | KIND OF EXCREMENT | AMOUNT OF URINATION | SHAPE OF DEFECATION | COLOR OF DEFECATION | EXCRE -TION COUNT | AGE | GENDER | ADDRESS (ZIP CODE) |
|---|---|---|---|---|---|---|---|---|---|
| 1 | 2019/7/1 6:24:30 | URINATION | NORMAL | | | 1 | | | |
| 2 | 2019/7/1 7:35:20 | DEFECATION | | NORMAL | BROWN | 2 | | | |
| 3 | 2019/7/1 9:15:10 | URINATION | NORMAL | | | 3 | | | |
| 4 | 2019/7/1 10:24:30 | URINATION | NORMAL | | | 4 | | | |
| 5 | 2019/7/1 12:12:56 | URINATION | GREAT | | | 5 | | | |
| 6 | 2019/7/1 14:23:34 | URINATION | NORMAL | | | 6 | | | |
| 7 | 2019/7/1 16:51:30 | URINATION | SMALL | | | 7 | | | |
| 8 | 2019/7/1 18:11:50 | URINATION | NORMAL | | | 8 | | | |
| 9 | 2019/7/1 20:14:10 | URINATION | NORMAL | | | 9 | | | |
| 10 | 2019/7/1 22:20:30 | URINATION | SMALL | | | 10 | | | |

| MONTH | SHAPE OF DEFECATION | | | | | | | | |
|---|---|---|---|---|---|---|---|---|---|
| | HARD | | | NORMAL | | | DIARRHEA | | |
| | COLOR | COLOR | COLOR | COLOR | COLOR | COLOR | COLOR | COLOR | COLOR |
| 1 | | | | | | | | | |
| 2 | | | | | | | | | |
| 3 | | | | | | | | | |
| 4 | | | | | | | | | |
| 5 | | | | | | | | | |
| 6 | | | | | | | | | |
| 7 | | | | | | | | | |
| 8 | | | | | | | | | |
| 9 | | | | | | | | | |
| 10 | | | | | | | | | |
| 11 | | | | | | | | | |
| 12 | | | | | | | | | |

Fig. 23

EXCREMENT ANALYSIS APPARATUS, ANALYSIS SYSTEM, SERVER APPARATUS, ANALYSIS METHOD, AND NON-TRANSITORY COMPUTER-READABLE MEDIUM

This application is a National Stage Entry of PCT/JP2021/019943 filed on May 26, 2021, which claims priority from Japanese Patent Application 2020-097575 filed on Jun. 4, 2020 and Japanese Patent Application 2020-179605 filed on Oct. 27, 2020, the contents of all of which are incorporated herein by reference, in their entirety.

TECHNICAL FIELD

The present disclosure relates to an excrement analysis apparatus, an analysis system, a server apparatus, and a program.

BACKGROUND ART

A caregiver who provides excretion assistance at a caregiving site is required to reduce incontinence of a care receiver and support independence of the care receiver while maintaining dignity of the care receiver. Since the excretion assistance at a caregiving site may damage dignity of the care receiver depending on occasions, a caregiver is forced to bear a heavy burden, and support for reducing a load of work is required.

Further, a caregiver may provide constant assistance by a carer before and after an excretion behavior when a care receiver is a person who needs assistance in leaving from a toilet seat or exiting from a toilet, and for a purpose of preventing an unexpected accident in the toilet. It can be said that a burden on the carer is also heavy in this point.

Work of a caregiver also includes work of creating an excretion diary in excretion assistance of a care receiver. Therefore, the caregiver obtains information to be written in the excretion diary by entering a toilet with a care receiver and observing an excretion behavior of the care receiver, or hearing from the care receiver.

The former is mainly performed for a care receiver from whom accurate information is not heard due to dementia and the like. In the former case, since observing an excretion behavior is a shame for the care receiver, it can be said that dignity of the care receiver is likely to be damaged, and observation in such a scene is a task that also imposes a burden on the caregiver.

Meanwhile, in the latter case, since an inaccurate application may also occur due to a sense of shame of a care receiver, it can be said that there is personality in an excretion record, and as a consequence, even though the care receiver performs the same excretion behavior, a difference may occur in a content of an excretion diary. With such a difference, it is difficult for a carer to accurately recognize health damage such as constipation and a urination disorder, and thus it may be late to handle the situation, or, even when a care receiver is not suffering from health damage, unnecessary administration of medicine such as a laxative may increase due to a false statement. Therefore, for covering such a difference, a burden related to excretion management and an excretion record on a carer increases.

Furthermore, when a care receiver has dementia, the care receiver mistakes a urine absorbing pad as a toilet paper during excretion or intentionally tries to hide an evidence of excretion failure (incontinence of feces and urine) due to his/her shame, thereby the urine absorbing pad may be flushed to a toilet. In such a case or on a regular basis, a care facility asks a contractor to perform drain pipe cleaning work, such as foreign body removal, in order to clear clogging of a drain pipe, and furthermore it is not possible to operate a drainage-related facility during the work. In order to solve such a problem, it is conceivable that a carer performs excretion end check and abnormality check related to excretion of a care receiver, but, even when the carer performs hearing later for an excretion diary, the carer always needs to wait beside a user in the end.

In order to improve such a situation, a mechanism for managing excretion of a user of a toilet by installing a sensor in the toilet and analyzing data acquired by the sensor has been proposed. For example, Patent Literature 1 describes a method being used for human excrement of a target person to be placed in a toilet bowl. In this method, light is received from the toilet bowl by using one or more optical sensors while the human excrement is placed in the toilet bowl, received light is analyzed by a computer processor, and thus one or more spectrum components indicating light absorption by a component of an erythrocyte are detected in the received light. Then, in this method, presence of blood is determined in the human excrement in response to the detection, and an output of an output device is generated at least partially in response to the determination. Further, Patent Literature 1 also describes that human excrement of a target person is monitored over a long period, an amount of blood detected in the human excrement is compared with a threshold amount over a certain period, and an alert is generated when a degree of bleeding indicates presence of cancer and/or a polyp.

Patent Document 2 describes an excretion notification system of a pet being connected to at least a user terminal and a pet toilet. When usage starts, the excretion notification system described in Patent Literature 2 acquires individual identification information including at least a name of a pet individual from the user terminal, and registers the individual identification information in association with an identifier of the pet. After usage starts, the excretion notification system acquires weight information of the pet individual from the pet toilet, stores the weight information in association with the identifier of the pet, and also calculates and registers a weight threshold, based on an average value of weight of the pet individual in a predetermined period. Furthermore, after usage starts, the excretion notification system acquires urination information of the pet individual from the pet toilet, calculates an average value of a urination count and an amount of urination of the pet individual in a predetermined period, and registers as a urination count threshold and a urination amount threshold, respectively. Then, when the weight information or the urination information of the pet individual being acquired from the pet toilet deviates from each threshold, the excretion notification system notifies alert information indicating that there is a possibility of a sign of predetermined pathology. Further, the excretion notification system includes a camera for determining an entry of the pet to the pet toilet.

Further, as a technique for recognizing a tendency of a daily change in an Na/K ratio in urine of a measured person, Patent Literature 3 describes a urine component analysis apparatus for a purpose of accurately acquiring the Na/K ratio in urine excreted by the measured person. This apparatus stores data representing a correlation between a statistical concentration ratio acquired by performing statistical processing on an Na/K ratio in urine excreted by a human for a plurality of times and the Na/K ratio in all urine in a single day or a plurality of days when all urine excreted by the human in the single day or the plurality of days is combined together. Further, on an assumption that the Na/K ratio in urine for one time excreted by the measured person is input for all of a plurality of time periods of a day, this apparatus performs statistical processing on the input Na/K ratio in the urine for a plurality of times of the measured person, and acquires a statistical concentration ratio. Then, this apparatus converts and acquires the Na/K ratio in all the urine in the single day or the plurality of days of the measured person by using the stored correlation, based on the statistical concentration ratio. Further, this apparatus successively stores the Na/K ratio in association with each of a urination date and time, a measurement date and time, and a time period of urination. Then, this apparatus reads the stored content, and thus a user can easily recognize a tendency of a daily change in the Na/K ratio in all the urine in the single day or the plurality of days of the measured person.

Further, as a technique for estimating a health state of a living body, Patent Literature 4 describes a data detection apparatus for purposes of acquiring biological data in a non-contact and non-invasive manner, and estimating a health state of a living body. This apparatus includes an image capturing unit that captures at least any one of an anus and its periphery of a living body, a private part and its periphery of the living body, and excrement of the living body, and includes a data analysis unit. The data analysis unit acquires biological data related to the anus, the private part, or a property and a condition of the excrement of the living body by an analysis of a capturing image by the image capturing unit, and estimates a health state of the living body from the biological data. Herein, the property and the condition of the excrement are at least any one of a color, a shape, a temperature, a light reflectance, and a light transmittance of the excrement.

Patent Literature 5 describes a biological information utilizing system for a purpose of efficiently collecting sufficient information in order to generate added value information with high accuracy. This system uses, as biological information, a body temperature, a protein concentration in urine, a glucose concentration in urine, an amino acid concentration in urine, and viscosity of feces. Further, this system generates the added value information including a value acquired by aggregating a certain measurement value in a period at a predetermined measurement date and time by residential district number associated with a subject identification number. Further, Patent Literature 5 describes that the value aggregated by residential district number is an average value of a body temperature by residential district, and the added value information is effective for an inspection when the added value information has a content of an average value acquired by aggregating, by residential district number, fever of subjects being collected. The inspection herein refers to an inspection of a geographical distribution of a degree of spread of an infectious disease such as influenza.

CITATION LIST

Patent Literature

[Patent Literature 1] Japanese Patent Application Publication (Translation of PCT Application) No. 2018-510334
[Patent Literature 2] Japanese Unexamined Patent Application Publication No. 2019-071896
[Patent Literature 3] Japanese Unexamined Patent Application Publication No. 2017-072410
[Patent Literature 4] Japanese Unexamined Patent Application Publication No. 2007-252805
[Patent Literature 5] Japanese Unexamined Patent Application Publication No. 2007-323528

SUMMARY OF INVENTION

Technical Problem

In the technique described in Patent Literature 1, presence of blood in excrement can only be determined, and a foreign body cannot be monitored and a state of excrement other than contamination of blood cannot also be recognized. Thus, the present applicant has considered that it is desirable to generate an excretion diary, based on imaging data in which excrement is captured by an image capture apparatus. Note that, the system described in Patent Literature 2 includes the camera, but the camera is used for monitoring a pet and is not used for capturing excrement.

However, a mental burden on a user of a toilet including a care receiver that his/her excretion behavior and excrement are captured by an image capture apparatus and managed is heavy. The mental burden is caused by a possibility that a third person may view acquired imaging data, and is related to privacy. Therefore, contrivance of reducing a mental burden of a toilet user by preventing imaging data about excrement from being seen by a third person while acquiring the imaging data with a toilet sensor is desired.

Furthermore, imaging data about excrement need to be accurately analyzed and recorded in order to generate an excretion diary, but there is also a scene where a notification to a carer is immediately needed even though an accurate analysis requires a lot of time and health damage of a user cannot also be recognized by excrement for one time.

For example, it is conceivable to acquire a high-grade analysis result by performing an analysis of imaging data by using a cloud service, but the imaging data are transmitted to a server apparatus that provides the service and the analysis result is waited, and thus an immediate notification to an observer such as a carer is difficult. Examples of a case where an immediate notification is needed include a notification of presence of a foreign body in order to remove the foreign body, a start notification of excretion, an end notification of excretion, and a notification of other abnormalities. Further, when the imaging data are transmitted to the server apparatus for an analysis, a mental burden related to privacy of a toilet user increases as described above.

On the other hand, when an analysis with speed and accuracy similar to those of the cloud service is to be achieved by only an apparatus installed in a toilet without using the cloud service, a calculator having specifications needed for the analysis needs to be installed. Note that, the calculator herein may refer to a central processing unit (CPU) and the like. However, it can be said that installing such a calculator is unrealistic in terms of problems such as a space, heat generation, and a price. Note that, the techniques described in Patent Literatures 3 to 5 cannot solve the problems as described above.

An object of the present disclosure is to provide an excrement analysis apparatus, an analysis system, a server apparatus, a program, and the like that solve the problems described above. The challenge is to be able to accurately collect information indicating a content of excrement excreted in a toilet bowl without having to ask a user of a toilet while considering privacy of the user of the toilet, and to be able to also handle a scene where an immediate notification to an observer is needed.

Solution to Problem

An excrement analysis apparatus according to a first aspect of the present disclosure includes: an input unit that inputs imaging data captured by an image capture apparatus installed in such a way as to include, in a capturing range, an excretion range of excrement in a toilet bowl of a toilet; a holding unit that temporarily holds imaging data input by the input unit; a first analysis unit that analyzes first analysis target data being imaging data input by the input unit, and outputs notification information to an observer who observes a user of the toilet; and a second analysis unit that analyzes second analysis target data being imaging data that is input by the input unit and temporarily held by the holding unit, and outputs detailed information indicating a content of excretion.

A server apparatus according to a second aspect of the present disclosure includes: a reception unit that receives detailed information indicating a content of excretion being a result of analyzing excrement in a toilet bowl of a toilet from imaging data captured in the toilet bowl; a storage unit that stores the detailed information received by the reception unit; and an information processing unit, wherein the detailed information includes at least information indicating an excretion date and time, a kind of excrement, and a shape of defecation, and the information processing unit aggregates the detailed information for each shape of the defecation.

A server apparatus according to a third aspect of the present disclosure includes: a reception unit that receives detailed information indicating a content of excretion being a result of analyzing excrement in a toilet bowl of a toilet from imaging data captured in the toilet bowl, user information that is associated with the detailed information and indicates a user of the toilet, address information that is associated with the detailed information and indicates an address where a user of the toilet lives or an address of an installation place of the toilet, and environmental information including weather information and infectious disease spread information indicating a result of spread of an infectious disease; a storage unit that stores the detailed information, the user information, the address information, and the environmental information being received by the reception unit; and an information processing unit, wherein the detailed information includes at least information indicating an excretion date and time, a kind of excrement, and a shape of defecation, and the information processing unit analyzes, from the user information, the address information, the environmental information, and the detailed information, a tendency of a time change in the defecation according to the environmental information for each user indicated by the user information, and predicts, from a result of an analysis, a health state including a morbidity state of the infectious disease for each user indicated by the user information.

An analysis method according to a fourth aspect of the present disclosure includes: an input step of, by an excrement analysis apparatus, inputting imaging data captured by an image capture apparatus installed in such a way as to include, in a capturing range, an excretion range of excrement in a toilet bowl of a toilet; a holding step of, by the excrement analysis apparatus, temporarily holding imaging data input in the input step; a first analysis step of, by the excrement analysis apparatus, analyzing first analysis target data being imaging data input in the input step, and outputting notification information to an observer who observes a user of the toilet; and a second analysis step of, by the excrement analysis apparatus, analyzing second analysis target data being imaging data that is input in the input step and temporarily held in the holding step, and outputting detailed information indicating a content of excretion.

An analysis method according to a fifth aspect of the present disclosure includes: a reception step of, by a server apparatus, receiving detailed information indicating a content of excretion being a result of analyzing excrement in a toilet bowl of a toilet from imaging data captured in the toilet bowl; a storage step of, by the server apparatus, storing the detailed information received in the reception step; an information processing step; and a provision step, wherein the detailed information includes at least information indicating an excretion date and time, a kind of excrement, and a shape of defecation, the information processing step includes, by the server apparatus, aggregating the detailed information for each shape of the defecation, and, the provision step includes, by the server apparatus, providing a processing result in the information processing step to an external apparatus.

A program according to a sixth aspect of the present disclosure is a program for causing a computer for control included in an excrement analysis apparatus to perform: an input step of inputting imaging data captured by an image capture apparatus installed in such a way as to include, in a capturing range, an excretion range of excrement in a toilet bowl of a toilet; a holding step of temporarily holding imaging data input in the input step; a first analysis step of analyzing first analysis target data being imaging data input in the input step, and outputting notification information to an observer who observes a user of the toilet; and a second analysis step of analyzing second analysis target data being imaging data that is input in the input step and temporarily held in the holding step, and outputting detailed information indicating a content of excretion.

A program according to a seventh aspect of the present disclosure is a program for causing a computer to perform: a reception step of receiving detailed information that indicates a content of excretion being a result of analyzing excrement in a toilet bowl of a toilet from imaging data captured in the toilet bowl, and includes at least information indicating an excretion date and time, a kind of excrement, and a shape of defecation; a storage step of storing the detailed information received in the reception step; an information processing step of aggregating the detailed information for each shape of the defecation; and a provision step of providing a processing result in the information processing step to an external apparatus.

Advantageous Effects of Invention

The present disclosure can provide an excrement analysis apparatus, an analysis system, a server apparatus, a program, and the like that solve the problems described above. In other words, the present disclosure is able to accurately collect information indicating a content of excrement excreted in a toilet bowl without having to ask a user of a toilet while considering privacy of the user of the toilet, and is able to also handle a scene where an immediate notification to an observer is needed.

BRIEF DESCRIPTION OF DRAWINGS

FIG. 5 is a diagram for describing a processing example in the excrement analysis apparatus in the excrement analysis system in FIG. 2;

FIG. 6 is a diagram for describing a processing example in the excrement analysis apparatus in the excrement analysis system in FIG. 2;

FIG. 7 is a diagram for describing a processing example in the excrement analysis apparatus in the excrement analysis system in FIG. 2;

FIG. 10 is a diagram illustrating one example of a feces characteristic analysis included in a non-real time analysis in the processing example in FIG. 9;

FIG. 11 is a diagram illustrating one example of a feces color analysis included in the non-real time analysis in the processing example in FIG. 9;

FIG. 12 is a diagram illustrating one example of a urination amount analysis included in the non-real time analysis in the processing example in FIG. 9;

FIG. 15 is a diagram illustrating one example of transmission information transmitted from an excrement analysis apparatus in the analysis system in FIG. 14;

FIG. 16 is a diagram illustrating one example of an intensive information table included in an excretion information database stored in a server apparatus in the analysis system in FIG. 14;

FIG. 17 is a diagram illustrating one example of an aggregate information table included in the excretion information database stored in the server apparatus in the analysis system in FIG. 14;

FIG. 18 is a diagram illustrating one example of an aggregate information table included in the excretion information database stored in the server apparatus in the analysis system in FIG. 14;

FIG. 19 is a diagram illustrating one example of an aggregate information table included in the excretion information database stored in the server apparatus in the analysis system in FIG. 14;

FIG. 22 is a diagram illustrating one example of an intensive information table included in an excretion information database stored in a server apparatus in the analysis system in FIG. 21;

FIG. 23 is a diagram illustrating one example of an aggregate information table included in the excretion information database stored in the server apparatus in the analysis system in FIG. 21;

EXAMPLE EMBODIMENT

Figure 1:
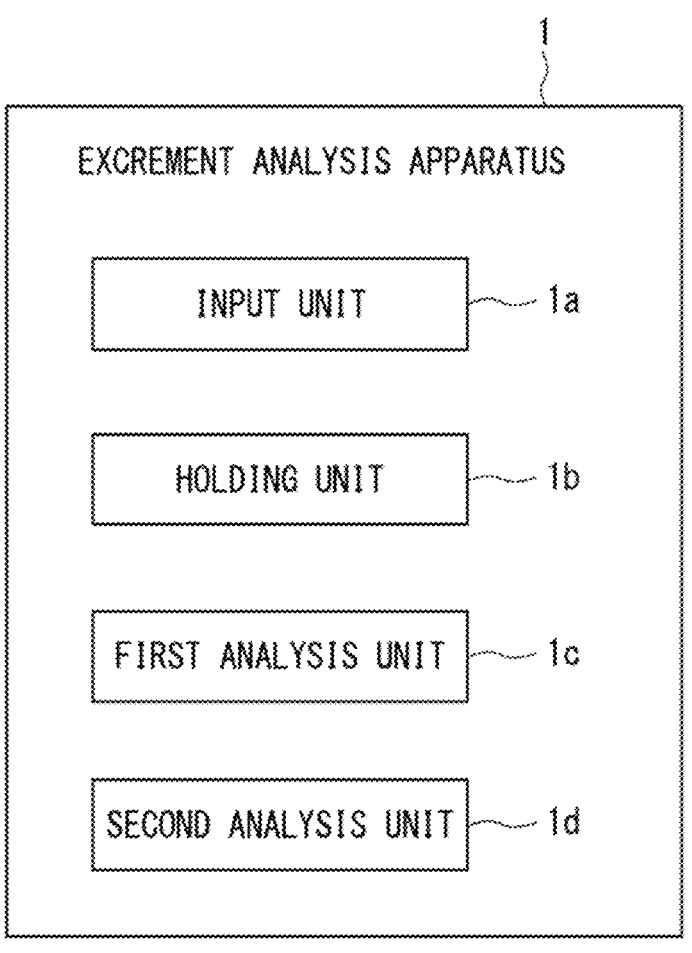
FIG. 1 is a block diagram illustrating one configuration example of an excrement analysis apparatus according to a first example embodiment.

Hereinafter, example embodiments will be described with reference to the drawings. In the example embodiments, the same or equivalent elements are given the same reference numerals and redundant description thereof will be omitted. Further, reference signs and names of elements in the drawings are provided to each element as one example to facilitate understanding for the sake of convenience and are not intended to limit any content of the present disclosure. Further, there are drawings in which arrows in one direction and two directions are drawn in the drawings described below, but both of the arrows clearly indicate a direction of a flow of a certain signal (data), and do not exclude unidirectional and bidirectional characteristics.

First Example Embodiment

An excrement analysis apparatus according to a first example embodiment will be described with reference to FIG. 1. FIG. 1 is a block diagram illustrating one configuration example of the excrement analysis apparatus according to the first example embodiment.

As illustrated in FIG. 1, an excrement analysis apparatus 1 according to the present example embodiment may include an input unit 1a, a holding unit 1b, a first analysis unit 1c, and a second analysis unit 1d.

The input unit 1a inputs imaging data (image data) captured by an image capture apparatus (hereinafter exemplified as a camera) installed in such a way as to include, in a capturing range, an excretion range of excrement in a toilet bowl of a toilet. The imaging data are used for analyzing a content of excrement and acquiring information about the content of the excrement in the excrement analysis apparatus 1.

Thus, the camera installed in such a manner is connected to or included in the excrement analysis apparatus 1. Note that, it can be said that it is preferable for the excrement analysis apparatus 1 to include the camera in terms of being integral with the apparatus and preventing an outflow of imaging data to the outside. The camera is not limited to a visible light camera, and may be an infrared light camera and the like, and may also be a video camera as long as a still image can be extracted. When the camera is connected to the outside of the excrement analysis apparatus 1, the camera may be connected to the input unit 1a. The imaging data may include additional information (attached information) such as a capturing date and time and a capturing condition. The capturing condition may include, for example, a resolution of a camera whose resolution can be set, and a zoom magnification in a case of a camera having a zoom function.

The excretion range described above may be a region including a stagnant part of the toilet bowl, and may also be referred to as a scheduled excretion range. By installing the camera in such a way as to include such an excretion range in the capturing range, captured imaging data include excrement and the like as subjects. Of course, the excretion range described above is preferably set in such a way that a user (a person who uses the toilet, and a user of the toilet) is not reflected, and the camera is preferably installed in such a way that a lens of the camera is also not seen by the user. Further, when the user uses the excrement analysis apparatus 1 in a hospital or a care facility, for example, the user described above is mainly a care receiver such as a patient. Further, examples of a carer include a caregiver, also include a doctor according to occasions, but may also include a helper other than a caregiver and may be other persons.

Hereinafter, information acquired from the excrement analysis apparatus 1 is referred to as excretion information. The excretion information is information indicating a content of excretion, and in a simpler example, can be information indicating whether excrement is feces (stool) or pee (urine). The excretion information may also include other information such as information indicating a color of excrement and a shape of a solid body if excrement is the solid body. Further, date and time information indicating a capturing date and time or an acquisition date and time of imaging data, and additional information such as a capturing condition may be included in or added to the excretion information.

Then, as described below, an analysis of a content of excretion is performed by the first analysis unit 1*c* and the second analysis unit 1*d*, but the holding unit 1*b* is included in order to temporarily hold data to be an analysis target in the second analysis unit 1*d*. In other words, the holding unit 1*b* temporarily holds the imaging data input in the input unit 1*a*. The holding unit 1*b* may be a storage apparatus such as a memory.

The first analysis unit 1*c* analyzes first analysis target data being the imaging data input in the input unit 1*a*, and outputs notification information to an observer who observes a user of the toilet. The notification information is a part of the excretion information, and is information that notifies a content according to an analysis result by the first analysis unit 1*c*. A specific example of the notification information will be described below, and the notification information may be information that makes a notification that a foreign body is mixed when the foreign body is captured in the imaging data, for example. Further, the notification information is information presented to an observer by being notified to the observer, and may thus also be referred to as presentation information. Further, the notification information may include information needed to be handled by an observer, and, in this case, may also be referred to as alert information. Since the first analysis unit 1*c* analyzes the imaging data input in the input unit 1*a*, the analysis performed herein corresponds to a real time analysis. Thus, the first analysis unit 1*c* may be referred to as a real time analysis unit.

Further, an output destination of the notification information by the first analysis unit 1*c* may be a terminal apparatus used by an observer, and a direct output destination may also be set to a server apparatus that can receive the notification information and transfer the notification to the terminal apparatus, and the like. Note that, the terminal apparatus used by an observer is not limited to a terminal apparatus used by an observer alone such as a carer, and may be, for example, a terminal apparatus installed at an observation station such as a nurse station, and the terminal apparatus may function as an alert apparatus. Further, the output destination of the notification information is not limited to one place.

Further, the imaging data input in the input unit 1*a* or the imaging data output from the input unit 1*a* to the holding unit 1*b* and the first analysis unit 1*b* on a subsequent stage may be, for example, data when an object is detected as a subject in the excretion range or a change such as a change in color of stagnant water is detected. These detections can be performed, for example, by performing capturing with the camera or the input unit 1*a* at all times or at regular intervals and using imaging data acquired through the capturing. Alternatively, capturing may be performed based on a user detection result from a separately provided user detection sensor (a load sensor provided on a toilet seat, other human detecting sensors, and the like), and imaging data at that time may also be selected as data to be output from the camera or the input unit 1*a* to the subsequent stage.

The second analysis unit 1*d* analyzes second analysis target data being the imaging data input in the input unit 1*a* and temporarily held in the holding unit 1*b*, and outputs detailed information indicating a content of excretion. The detailed information is a part of the excretion information, and is information that indicates a content according to an analysis result by the second analysis unit 1*d*. The detailed information is information indicating a more specific content than the notification information, and may be information indicating a feces characteristic, a feces amount, a feces color, a urine amount, a urine color, and the like, for example, in which a specific example thereof will be described below. Since the second analysis unit 1*d* analyzes the imaging data held in the holding unit 1*b*, the analysis performed herein corresponds to a non-real time analysis. Thus, the second analysis unit 1*d* may be referred to as a non-real time analysis unit.

Further, an output destination of the detailed information by the second analysis unit 1*d* may be set to a server apparatus that collects and manages the excretion information, and the server apparatus may be, for example, a cloud server apparatus. The server apparatus can be installed in a facility such as a hospital in a case of the facility, and can also be installed in a private house or installed in an apartment house in a case of a private use. Further, the output destination of the detailed information is not limited to one place.

The excrement analysis apparatus 1 may include a communication unit that is not illustrated, and the communication unit may also be provided in each of the first analysis unit 1*c* and the second analysis unit 1*d*. The communication unit may be formed of a wired or wireless communication interface and the like, for example.

The excrement analysis apparatus 1 may include a control unit (not illustrated) that controls the entire excrement analysis apparatus 1, and the control unit may also include a part of the input unit 1*a*, the holding unit 1*b*, the first analysis unit 1*c*, and the second analysis unit 1*d* described above. The control unit can be implemented by, for example, a central processing unit (CPU), a working memory, a nonvolatile storage apparatus that stores a program, and the like. The program may be a program for causing the CPU to perform the processing of each of the units 1*a* to 1*d*. Further, the holding unit 1*b* can also use the storage apparatus, but can also include a different storage apparatus. Further, the control unit included in the excrement analysis apparatus 1 can also be implemented by, for example, an integrated circuit.

Further, the excrement analysis apparatus 1 is an apparatus that analyzes a content of excrement excreted in a toilet and outputs the excretion information as described above, and may also be referred to as a toilet excrement analysis apparatus or an excretion information acquisition apparatus. The excrement analysis apparatus 1 may be an apparatus for functioning as a toilet sensor being an edge in an excrement analysis system (analysis system) constituted on a network by including a terminal apparatus of an observer, an external server apparatus, and the like.

As described above, the excrement analysis apparatus 1 divides an analysis of imaging data acquired from the camera into a real time analysis for a notification purpose and a non-real time analysis for a recording purpose. In this way, the excrement analysis apparatus 1 can achieve space saving and energy saving of the control unit such as a built-in CPU. This means that the excrement analysis apparatus 1 efficiently uses a limited calculation resource by dividing analysis processing into a function that requires immediacy and the other function. Furthermore, the excrement analysis apparatus 1 does not need to transmit imaging data acquired from the camera and the other image data to the outside such as a cloud, and can perform an analysis of excrement by its own apparatus installed in a toilet. In other words, all of an image and a video used for an analysis in the excrement analysis apparatus 1 are processed in the excrement analysis apparatus 1, and the image and the video are not transmitted to the outside. Therefore, it can be said that the excrement analysis apparatus 1 has a configuration that leads to a reduction in a mental burden related to privacy of a user.

As described above, the excrement analysis apparatus 1 can accurately collect information indicating a content of excrement excreted in a toilet bowl without having to ask a user of a toilet while considering privacy of the user of the toilet, and can also handle a scene where an immediate notification to an observer is needed. In other words, the excrement analysis apparatus 1 can achieve both of consideration for privacy of a user of a toilet, and notifying and recording while improving installation of a sensor in a toilet for reducing a burden on excrement management in monitoring such as nursing care. The notifying and recoding herein are notifying of an immediate event at a monitoring site such as a caregiving site and recoding of accurate information. Thus, the excrement analysis apparatus 1 can reduce a physical/mental burden on an observer and a toilet user.

Second Example Embodiment

Figure 2:
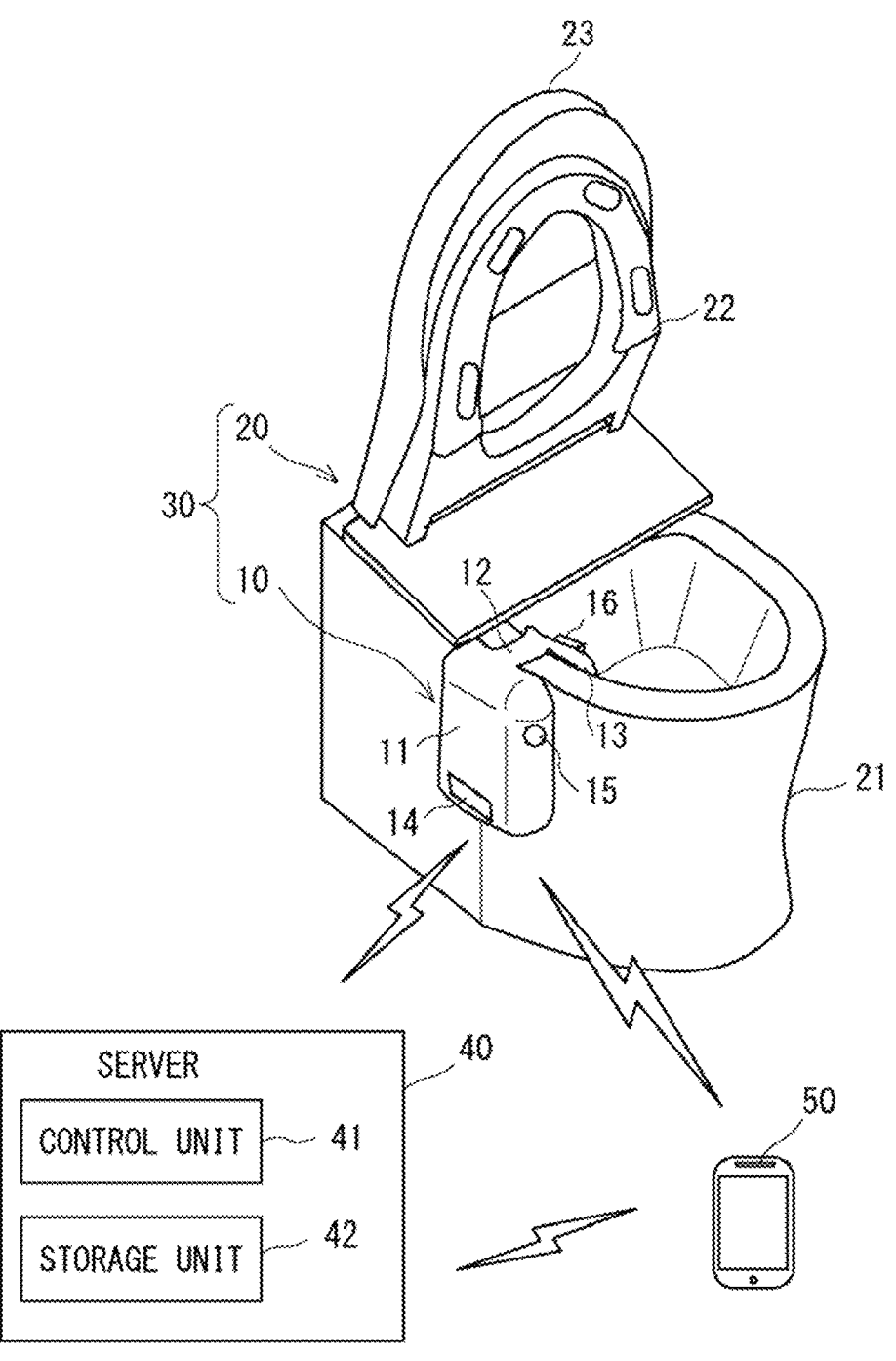
FIG. 2 is a diagram illustrating one configuration example of an excrement analysis system according to a second example embodiment.
Figure 3:
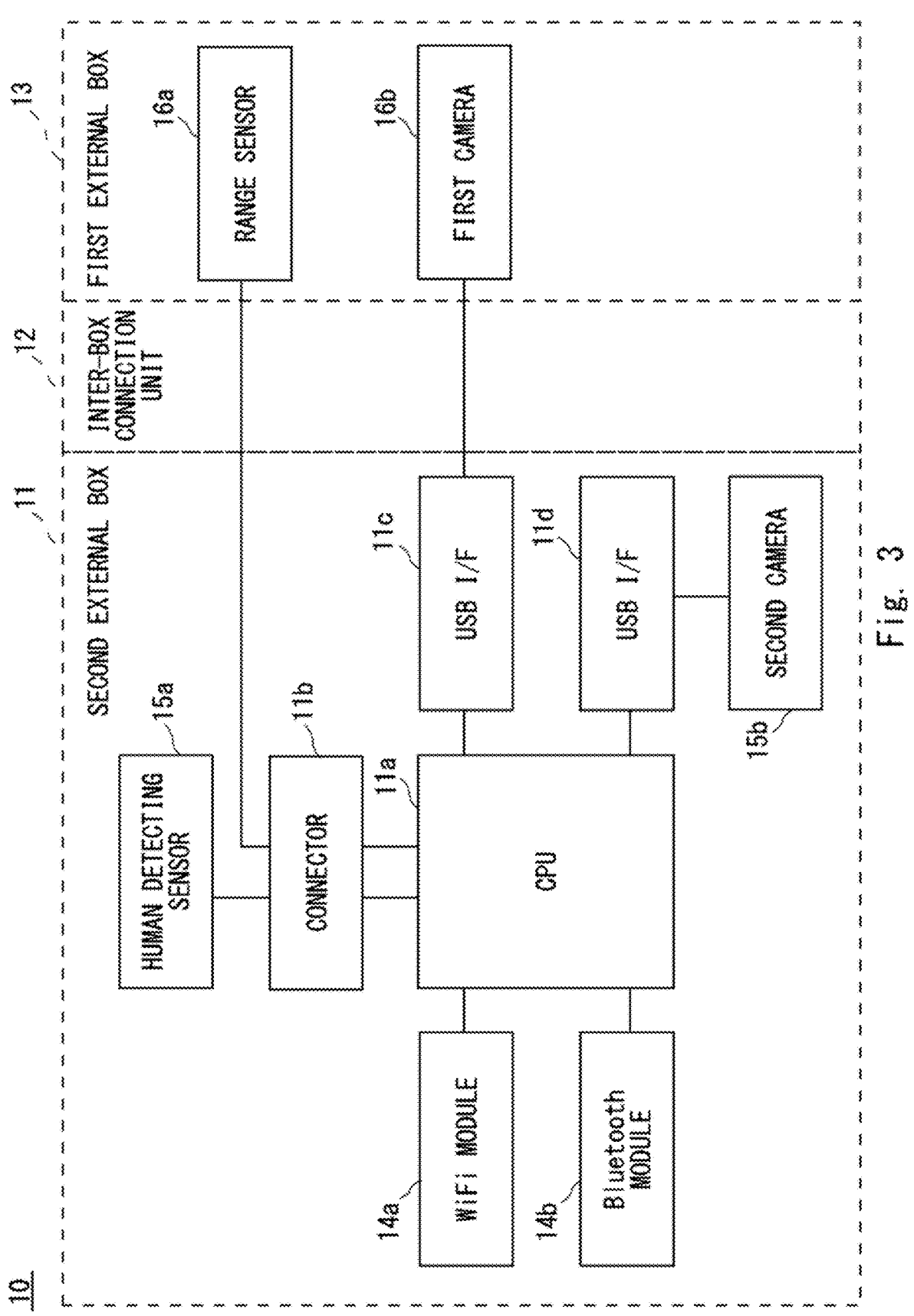
FIG. 3 is a block diagram illustrating one configuration example of an excrement analysis apparatus in the excrement analysis system in FIG. 2.

A second example embodiment will be mainly described with reference to FIGS. 2 to 12 while focusing on differences with the first example embodiment, but various examples described in the first example embodiment can be applied. FIG. 2 is a diagram illustrating one configuration example of an excrement analysis system according to the second example embodiment, and FIG. 3 is a block diagram illustrating one configuration example of an excrement analysis apparatus in the excrement analysis system in FIG. 2.

The excrement analysis system (hereinafter, the present system) according to the present example embodiment may include an excrement analysis apparatus 10 attached to a toilet bowl 20, a terminal apparatus 50 used by a carer, and a server apparatus (hereinafter, a server) 40. Note that, since the carer observes a user of a toilet, it can be said that the carer is one example of an observer.

The excrement analysis apparatus 10 is one example of the excrement analysis apparatus 1 and is exemplified as a toilet-bowl installation type apparatus, but may be installed in a toilet. Further, the toilet bowl 20 may include, on a main body 21, a toilet seat 22 having a hot water washing function for user washing and a toilet seat cover 23 for closing the toilet seat 22, for example. The excrement analysis apparatus 10 and the toilet bowl 20 can form a toilet bowl 30 with an analysis function of performing an analysis and outputting a result of the analysis.

Further, a shape of the excrement analysis apparatus 10 is not limited to the shape illustrated in FIG. 2, and may be configured such that all or some of the functions of the excrement analysis apparatus 10 are embedded in the toilet seat 22 and the like, for example. Further, some of the functions of the excrement analysis apparatus 10 may also be provided on the toilet seat 22 side. For example, when the excrement analysis apparatus 10 is not provided with a range sensor 16a to be described below and the toilet seat 22 is provided with a weight sensor, it is also possible to adopt a configuration in which the excrement analysis apparatus 10 receives information from the weight sensor by wireless or wired communication. Note that, the weight sensor may also be provided in an inter-box connection unit 12 described below, and may also simply be a pressure sensor that detects fixed pressure or more. Further, when the excrement analysis apparatus 10 is not provided with a first camera 16b to be described below and the toilet seat 22 side is provided with a camera, it is also possible to adopt a configuration in which the excrement analysis apparatus 10 receives imaging data from the camera by wireless or wired communication.

The server apparatus (server) 40 and the terminal apparatus 50 can be wirelessly connected to the excrement analysis apparatus 10, and the terminal apparatus 50 can be wirelessly connected to the server 40. Note that, these components may be connected to one another within, for example, one wireless local area network (LAN), but it is also possible to adopt another connection form such as connection in different networks. Further, a part or the whole of the connection may be performed in a wired manner.

In the present system connected in such a manner, the excrement analysis apparatus 10 outputs notification information by transmitting the notification information to the terminal apparatus 50, and outputs detailed information by transmitting the detailed information to the server 40. The terminal apparatus 50 is a terminal apparatus owned by a carer of a user of the toilet and may be a portable excrement analysis apparatus, but may be an installation type apparatus. In the former case, the terminal apparatus 50 may be a mobile phone (also including a smartphone), a tablet, a mobile PC, and the like. The server 40 may be an apparatus that collects and manages excretion information including the detailed information, and stores the detailed information received from the excrement analysis apparatus 10 in a viewable state from the terminal apparatus 50.

Further, the server 40 may include a control unit 41 that controls the entire server 40, a storage unit 42 that stores the detailed information in a database (DB) form, for example, and a communication unit (not illustrated) for performing the connection as described above. The control unit 41 performs control on storing of the detailed information transmitted from the excrement analysis apparatus 10 into the storage unit 42, control on viewing from the terminal apparatus 50, and the like. The control unit 41 can be implemented by, for example, a CPU, a working memory, a nonvolatile storage apparatus that stores a program, and the like. The storage apparatus can be shared with the storage unit 42, and the program may be a program for causing the CPU to implement the function of the server 40. Note that, the control unit 41 can also be implemented by, for example, an integrated circuit.

Further, although not illustrated, the terminal apparatus 50 may include a control unit that controls the entire terminal apparatus 50, a storage unit, and a communication unit for performing the connection as described above. Similarly to the control unit 41, the control unit can be implemented by, for example, a CPU, a working memory, a nonvolatile storage apparatus that stores a program, and the like, or an integrated circuit. Further, the program stored in the storage apparatus may be a program for causing the CPU to implement the function of the terminal apparatus 50.

Further, the terminal apparatus 50 preferably includes a diary generation unit that generates an excretion diary, based on the notification information received from the excrement analysis apparatus 10 and the detailed information stored in the server 40. The diary generation unit can be mounted by, for example, incorporating a diary generation application program into the terminal apparatus 50, and the like. The generated excretion diary can be stored in an internal storage unit. Further, the diary generation unit can also be mounted as a part of a care recording unit that generates a care record. The care recording generation unit can also be implemented by incorporating an application program into the terminal apparatus 50.

Next, a detailed example of the excrement analysis apparatus 10 will be described. The excrement analysis apparatus 10 may be formed of, for example, two apparatuses as illustrated in FIG. 2 and FIG. 3. More specifically, the excrement analysis apparatus 10 may include, as its housing, two boxes, for example, a first external box 13 and a second external box 11. Further, the excrement analysis apparatus 10 may include the inter-box connection unit (inter-box connection structure) 12 that connects the first external box 13 and the second external box 11. The first external box 13 and the second external box 11 can be connected by an interface having a specific example thereof as illustrated in FIG. 3.

In this example, the excrement analysis apparatus 10 may be installed on the main body 21 of the toilet bowl 20 as follows, for example. In other words, the excrement analysis apparatus 10 may be installed on the toilet bowl 20 by placing the inter-box connection unit 12 on the edge of the main body 21 in such a way that the first external box 13 is arranged on the inside of the main body 21 (side where an excretion range of excrement is located) and the second external box 11 is arranged on the outside of the main body 21.

The first external box 13 may accommodate, for example, the range sensor 16a and the first camera 16b. As described below, the range sensor 16a is one example of a sitting sensor that detects that sitting is performed on the toilet seat 22, and the first camera 16b is a camera that captures an image of excrement.

The second external box 11 includes an apparatus that performs a real time analysis being performed based on imaging data (image data) captured by the first camera 16b, and a non-real time analysis being performed based on the image data and a real time analysis result. Further, the second external box 11 includes a communication apparatus 14 that, under the control of the apparatus, makes a notification to a carer at occurrence of an event and transmits an analysis result to the server 40.

For example, the second external box 11 may accommodate a CPU 11a, a connector 11b, USB I/Fs 11c and 11d, a WiFi module 14a, a Bluetooth module 14b, a human detecting sensor 15a, and a second camera 15b. Note that USB is an abbreviation for universal serial bus, and USB, WiFi, and Bluetooth are all registered trademarks (the same applies below). The communication apparatus 14 exemplifies each of the modules 14a and 14b, and the CPU 11a performs a real time analysis and a non-real time analysis while transmitting and receiving data to and from another portion via each of the elements 11b, 11c, and 11d as necessary. Note that, in this example, description is given on an assumption that a memory as an example of the holding unit 1b is also included in the CPU 11a. Further, the second external box 11 is not provided with various I/Fs or connectors and may also be directly connected to the CPU 11a. Further, the communication apparatus 14 is not limited to the communication module of the exemplified standards regardless of wireless or wired. Examples of the communication module include, for example, various modules such as a long term evolution (LTE) communication module, a fifth generation mobile communication module, and a low power, wide area (LPWA) communication module.

As illustrated in FIG. 3, the first external box 13 and the second external box 11 are connected by the connector 11b and an interface exemplified by the USB I/F 11c, and the connection line is provided inside the inter-box connection unit 12, which configures one excrement analysis apparatus 10.

The first external box 13 will be described.

The range sensor 16a is a sensor that measures a distance to a target object (buttocks of a user of the toilet bowl 20) and detects that a user is sitting on the toilet seat 22, and detects that the target object is sitting on the toilet seat 22 when a certain time elapses beyond a threshold. Furthermore, when there is a change in the distance to the target object after sitting, the range sensor 16a detects that the user has left the toilet seat 22.

As the range sensor 16a, for example, an infrared sensor, a ultrasonic sensor, an optical sensor, and the like can be adopted. When an optical sensor is adopted as the range sensor 16a, it is sufficient that a transmission/reception element is disposed in such a way that light (not limited to visible light) can be transmitted/received from a hole provided in the first external box 13. In the transmission/reception element, a transmission element and a reception element may be configured separately or may be integrated. The range sensor 16a is connected to the CPU 11a via the connector 11b and may transmit a detection result to the CPU 11a side.

The first camera 16b is an example of a camera that captures imaging data input to the input unit 1a in FIG. 1, and may be an optical camera whose lens portion is disposed in the hole provided in the first external box 13. As described in the first example embodiment, the first camera 16b is installed in such a way as to include, in a capturing range, an excretion range of excrement in the toilet bowl 20 of the toilet. The first camera 16b is connected to the CPU 11a via the USB I/F 11c and transmits the imaging data to the CPU 11a side.

The second external box 11 will be described.

The CPU 11a is an example of a main control unit of the excrement analysis apparatus 10, and controls the entire excrement analysis apparatus 10. As described below, a real time analysis and a non-real time analysis are performed by the CPU 11a. The connector 11b connects the human detecting sensor 15a and the CPU 11a, and connects the range sensor 16a and the CPU 11a. The USB I/F 11c connects the first camera 16b and the CPU 11a, and the USB I/F 11d connects the second camera 15b and the CPU 11a.

The human detecting sensor 15a is a sensor that detects presence of a person (entry and exit of a person) in a specific region (measurement region range of the human detecting sensor 15a), and the specific region may be a region in which an entry/exit to and from a toilet can be determined. As the human detecting sensor 15a, for example, an infrared sensor, a ultrasonic sensor, an optical sensor, and the like can be adopted regardless of the detection method. The human detecting sensor 15a is connected to the CPU 11a via the connector 11b, and when a person is detected in the specific region, the human detecting sensor 15a transmits a detection result to the CPU 11a.

The CPU 11a may control an operation of the range sensor 16a and an operation of the first camera 16b, based on the detection result. For example, the CPU 11a may also perform processing of operating the range sensor 16a when the detection result indicates an entry, operating the first camera 16b when the range sensor 16a detects sitting, and the like.

The second camera 15b may be an optical camera whose lens portion is disposed in a hole provided in the second external box 11, and is an example of a camera that acquires face image data by capturing a face image of a user of the toilet in order to identify the user. The second camera 15b may be installed on the toilet bowl 20 in such a way as to include a face of a user in a capturing range, but may also be installed in a toilet room where the toilet bowl 20 is installed.

The Bluetooth module 14b is an example of a receiver that receives identification data for identifying a user from a Bluetooth tag held by the user, and may also be replaced with a module on the basis of another near-field communication standard. The Bluetooth tag held by the user may be set as a different ID for each user, and may be held by the user by being embedded in a wristband and the like, for example.

The WiFi module 14a is an example of a communication apparatus that transmits various types of data including the notification information to the terminal apparatus 50 and transmits various types of data including the detailed information to the server 40, and may also be replaced with a module adopting another communication standard. The face image data acquired by the second camera 15b and the identification data acquired by the Bluetooth module 14b may be added to or embedded in the notification information and the detailed information, and may be transmitted to the terminal apparatus 50 and the server 40, respectively. The terminal apparatus 50 and the server 40 that receive the face image data can perform face authentication processing, based on the face image data, and identify the user. However, the excrement analysis apparatus 10 can also be configured in such a way as not to transmit the face image data, and, in that case, user identification by face authentication can be achieved by causing the CPU 11a to perform the face authentication processing, and identification data indicating a result of the user identification can be set as a target of transmission.

The USB I/F 11c, or the CPU 11a and the USB I/F 11c may be one example of the input unit 1a in FIG. 1, and input imaging data captured by the first camera 16b. The CPU 11a and the WiFi module 14a may be one example of the first analysis unit 1c in FIG. 1, and the CPU 11a performs a real time analysis on the imaging data and transmits the notification information to the terminal apparatus 50 via the WiFi module 14a. Note that, the notification information can also be transmitted via the Bluetooth module 14b and the like. In this way, the notification information can be output by being transmitted to the terminal apparatus 50 connected to the excrement analysis apparatus 10 via a network or a near-field wireless communication network. Of course, the transmission herein may be transmission via the server 40 or another server as long as a transfer to the terminal apparatus 50 is performed. It is assumed that the notification information to be transmitted does not include the imaging data themselves, and thus not only a mental burden related to privacy of a user can be reduced, but also the amount of transmission data can also be reduced. Note that, additional information (such as a capturing date and time) of the imaging data can be set as a transmission target.

Note that, a smartphone is illustrated as an example of the terminal apparatus 50, but the notification destination (transmission destination) may be, for example, a notification apparatus of a nurse call system, another terminal apparatus owned by a carer, an intercom, and the like. Examples of the another terminal apparatus include, for example, a personal handy-phone system (PHS) and the like.

Further, the CPU 11a includes a storage apparatus such as a memory and may be one example of the holding unit 1b in FIG. 1, and holds the input imaging data and a result of the real time analysis. Further, the CPU 11a and the WiFi module 14a may be one example of the second analysis unit 1d in FIG. 1, and the CPU 11a performs a non-real time analysis on the held data and transmits the detailed information to the server 40 via the WiFi module 14a. In this way, the detailed information can be output by being transmitted to the server 40 connected to the excrement analysis apparatus 10 via a network. It is assumed that the detailed information to be transmitted does not include the imaging data themselves, and thus not only a mental burden related to privacy of a user can be reduced, but also the amount of transmission data can also be reduced. Note that, additional information (such as a capturing date and time) of the imaging data can be set as a transmission target. In this way, privacy of a user can be protected by not outputting the imaging data themselves to the outside of the excrement analysis apparatus 10.

Figure 4:
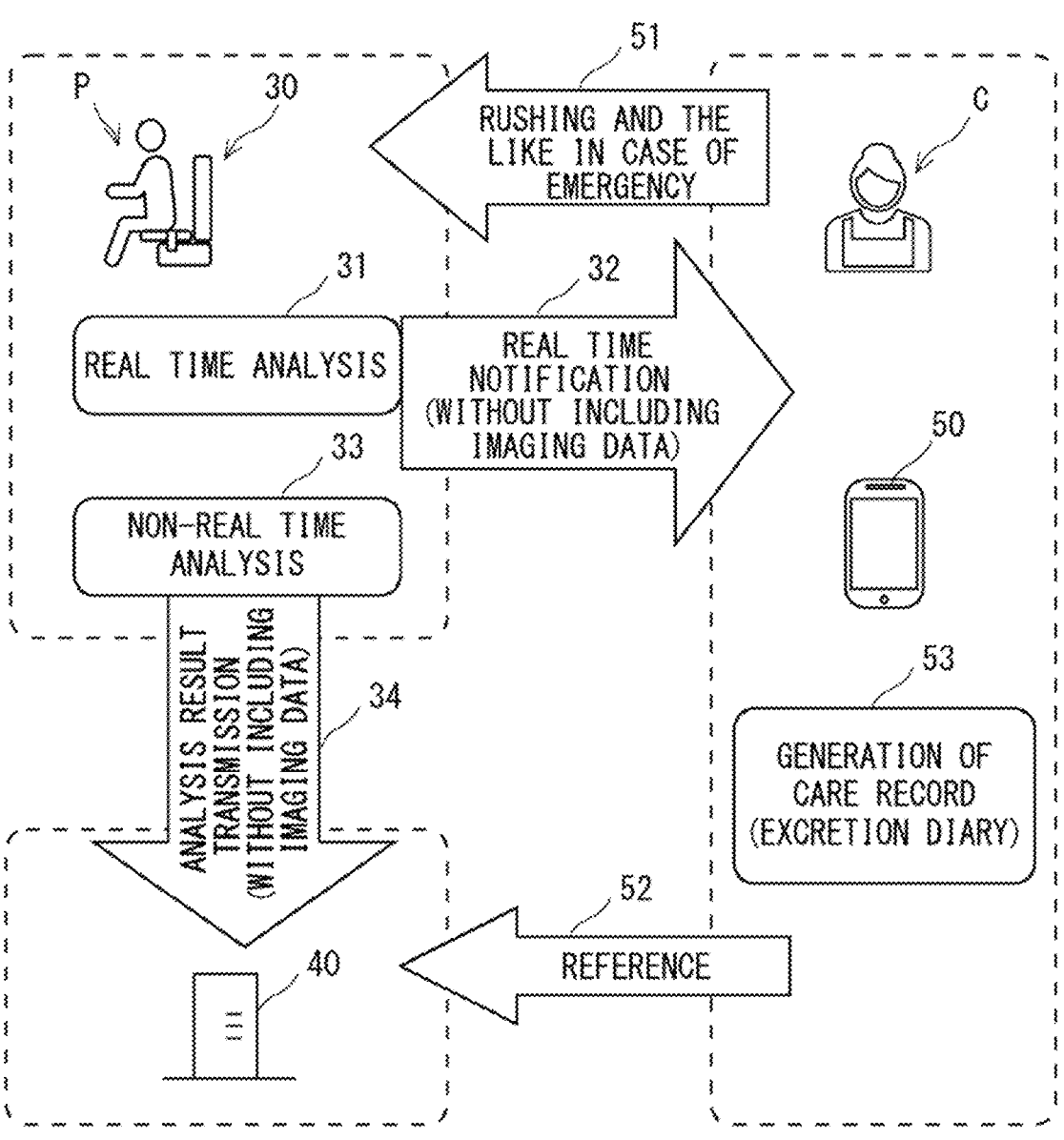
FIG. 4 is a schematic diagram for describing a processing example in the excrement analysis system in FIG. 2.

With reference to FIGS. 4 and 5, a real time analysis and a non-real time analysis will be schematically described. FIG. 4 is a schematic diagram for describing a processing example in the present system, and FIG. 5 is a diagram for describing a processing example in the excrement analysis apparatus 10.

As illustrated in FIG. 4, an example in which a user P uses the toilet bowl 30 with the analysis function being installed in a toilet, and a carer C of the user P monitors the state is given. When the user P uses the toilet bowl 30 with the analysis function, the CPU 11a detects that the user sits on a toilet seat, based on a detection result from the range sensor 16a functioning as a sitting sensor. When the CPU 11a detects sitting, the CPU 11a instructs the first camera 16b to start capturing, and performs a real time analysis 31, based on captured imaging data. The CPU 11a can perform a foreign body determination as the real time analysis 31. More specifically, the CPU 11a can perform an analysis of whether a foreign body being an object other than feces and urine is included as a subject except for the toilet bowl and washing liquid for the toilet bowl. Note that, the foreign body may also be referred to as another object, may be liquid or solid as long as it is other than feces and urine, and may include, for example, any one or more of vomit, melena, blood vomiting (hematemesis), a urine absorbing pad, a diaper, and a toilet paper core.

When the CPU 11a needs an immediate notification to the carer due to foreign body detection as a result of the real time analysis 31, the CPU 11a transmits notification information (a real time notification 32) to the terminal apparatus 50 of the carer C at a place away from the toilet via the WiFi module 14a. In this way, the CPU 11a can transmit foreign body information indicating whether the foreign body is included (foreign body information indicating a foreign body determination result) to the terminal apparatus 50. The foreign body information is output as a part of the notification information.

In this way, the carer C can be released from a situation where the carer C constantly stays with the user P during excretion of the user P, and can also take a measure 51 by rushing and the like in case of emergency by the real time notification 32. Herein, the real time notification 32 to be transmitted does not include imaging data.

The CPU 11*a* performs a non-real time analysis 33 being a more detailed excrement analysis, based on the held imaging data and a real time analysis result, after the real time analysis 31 ends. Thus, the holding unit in the CPU 11*a* temporarily holds the real time analysis result as a part of the second analysis target data. The CPU 11*a* performs transmission 34 of a non-real time analysis result to the server 40 via the WiFi module 14*a*.

Further, the carer C of the user P performs generation 53 of a care record (excretion diary) of the user P while appropriately performing reference 52 to detailed information about the user P being stored in the server 40, based on the received notification information, in the terminal apparatus 50. The excretion diary can be generated as a part of the care record. In this way, the excretion diary for each user can be recorded in the terminal apparatus 50. Note that, a format and the like of the excretion diary are not limited.

In this way, the analysis results of the real time analysis 31 and the non-real time analysis 33 are transmitted to the server 40 by the analysis result transmission 34 being performed by a communication function. The analysis result transmission 34 is transmitted without including the imaging data. The information recorded in the server 40 can be set as a target of the reference 52 for generation of the care record (excretion diary) 53 by the carer C and future care support.

With reference to FIGS. 5 to 7, a content of the real time analysis 31 and the non-real time analysis 33 will be described. FIGS. 5 to 7 are diagrams for describing a processing example in the excrement analysis apparatus 10.

First, one example of an input, a technique, and an output of the real time analysis and the non-real time analysis will be described with reference to FIG. 5. The real time analysis is an analysis that requires real time property, such as a notification to the carer C. For the real time analysis, data (imaging data) of an image captured by the first camera 16*b* can be an input and be classified into any of the following six kinds by deep learning (DL), for example, and a classification result can be an output. The six kinds are a foreign body (such as a diaper and a urine absorbing pad), feces, feces+urine, urine, urine dripping, and a buttocks washing apparatus (buttocks washing machine).

The DL technique can be used for comparing an image (background image) before excretion and the like with an image (image during excretion or after excretion is completed) after the excretion. For example, a background image and an image after excretion are input as an input to a learning model, and which of the six kinds the image corresponds to can be output. Alternatively, a difference image of an image after excretion from a background image is acquired as preprocessing, the difference image is input to a learning model, and thus which of the six kinds the image corresponds to can be output. Note that, when the image is classified into the buttocks washing machine, it can be determined that the excretion is completed. The classification kinds are an example of a phenomenon being a trigger of the real time notification.

In this way, in the real time analysis, the notification information can be acquired from the first analysis target data by using a learned model that inputs the first analysis target data and outputs the notification information. The notification information can be, for example, predetermined information associated with a classification result of the notification information. In this way, in the excrement analysis apparatus 10, information such as, for example, a start and completion of excretion, and contamination with a foreign body into excrement can be notified as the notification information to a carer and the like, and the carer and the like can acquire the information in real time. Note that, the learned model may be generated by machine learning, regardless of an algorithm (machine learning algorithm), hyper parameters such as the number of layers, and the like of the learned model. Further, presence or absence of training data is not limited in the machine learning. Further, the learned model used in the real time analysis may be plural, and, for example, different learned models can also be used for at least one kind of the six kinds described above and the other kinds.

In the non-real time analysis, for example, an analysis can be performed by two techniques of DL and image processing (IP) with the imaging data from the first camera 16*b* and a real time analysis result as an input. For example, an analysis using DL can output a feces characteristic, and an analysis using IP can output a feces color, a feces amount, a urine color, and a urine amount. Note that, herein, the real time analysis is handled as preprocessing of the non-real time analysis. In the non-real time analysis, a feces characteristic, a feces color, and the like are output by using DL and IP and comparing an analysis result (may be an image) subjected to the preprocessing with learned data.

Herein, the DL technique can also be used for comparing an image (background image) before excretion and the like with an image (image during excretion or after excretion is completed) after the excretion. For example, a classification result in the real time analysis, a background image, and an image after excretion are input as an input to a learning model, and a feces characteristic can be output. Alternatively, a difference image of an image after excretion from a background image is acquired as preprocessing, a classification result in the real time analysis and the difference image are input to a learning model, and thus a feces characteristic can be output. Further, only when a classification result in the real time analysis includes feces, an analysis by DL in the non-real time analysis may be performed, and, in that case, the classification result described above is unnecessary for an input to the learned model. Further, a processing method in IP is not limited, and required detailed information may be acquired. For example, matching processing with a comparison target image being stored in advance is performed by extracting a feature of an image and the like, and a feces color and the like indicated by the comparison target image having a high coincidence rate can be output. Note that, in the non-real time analysis, all outputs may be acquired by one of IP and DL.

In this way, in the non-real time analysis, at least a part of the detailed information can be acquired from the second analysis target data by using a learned model that inputs the second analysis target data (that may include a real time analysis result) and outputs the detailed information. Note that, the learned model may be generated by machine learning, regardless of an algorithm (machine learning algorithm), hyper parameters such as the number of layers, and the like of the learned model. Further, presence or absence of training data is not limited in the machine learning. Further, the learned model used in the real time analysis may be plural. Furthermore, as described above, in the non-real time analysis, at least a part of the detailed information can be acquired by performing image processing on the second analysis target data. As described above, a method of the image processing and the like are not limited, and required detailed information may be acquired.

With reference to FIG. 6, a detailed example of the real time analysis is illustrated. In the real time analysis, a foreign body, a kind of excrement, and a buttocks washing machine can be set as a target of a determination. First, foreign body detection is performed based on an image (imaging data) captured by the first camera 16b being an optical camera. The foreign body detection can be always performed, and a carer is notified at a time of the foreign body detection. Subsequently, a determination of feces, feces+urine, urine, and urine dripping is performed by DL based on a preprocessing image (and/or additional information) acquired by setting an image captured at a timing of sitting as a background image and then performing preprocessing on an image captured in a fixed cycle. The determination is performed until a timing at which sitting ends. The additional information herein can also include additional information exemplified by a capturing date and time and the like, and can also be, for example, information indicating a statistic in consideration of the fixed cycle described above, information indicating an area such as dimensions, and the like. Further, detection of a buttocks washing machine is also performed by a similar method at a similar timing, and the determination of feces, feces+urine, urine, and urine dripping ends at a timing at which the buttocks washing machine is detected.

In this way, the CPU 11a may transmit, as a real time analysis result, at least one piece of information indicating a usage situation of a buttocks washing machine installed in a toilet bowl and information indicating that sitting is performed on the toilet bowl as at least a part of the notification information to the terminal apparatus 50. As described above, the information indicating a usage situation of a buttocks washing machine can be acquired as a real time analysis result of imaging data. The reason is that a nozzle that ejects washing liquid or the washing liquid itself is included as a subject of the imaging data during use. Further, the information indicating that sitting is performed on a toilet bowl can be acquired by the sitting sensor exemplified by the range sensor 16a. In this way, the real time analysis can also be performed by also using information other than the imaging data. Note that, a usage situation of a buttocks washing machine can also be recognized by the CPU 11a by, for example, being connected to the buttocks washing machine and acquiring information from that instead of an analysis of the imaging data.

With reference to FIG. 7, a detailed example of the non-real time analysis is illustrated. For the non-real time analysis, an analysis can be performed on all targets being subjected to the preprocessing in the real time analysis by a selection of a background image and an input image. The selection of a background image and an input image has combinations each suitable for a determination target, and thus a detailed analysis is performed. To describe a combination example, for a feces characteristic, first, an image after sitting is selected as a background image, and a last feces image is selected as an input image. In a case of only feces or a case of only urine, a target image is also similarly selected for a feces color, a feces amount, and a urine color. However, a urine image is used instead of a feces image for a urine color. In a case of feces+urine, a last urine image before urine/feces is used as a background image, and a last urine/feces image is used as an input image. For a urine amount, a background image is not used, and all image determined to be urine dripping is used as an input image.

Herein, an example in which information indicating the amount of urination and the amount of defecation are output as the detailed information in the non-real time analysis is given, but the detailed information is not limited thereto. In the non-real time analysis, information about at least one of a urine flow rate or the amount of urination, a defecation count or the amount of defecation per unit time, and an excretion timing being a timing of an excretion behavior can be output as the detailed information. Particularly, in the non-real time analysis, information indicating at least one of a decrease situation of a urine flow rate or the amount of urination, a decrease situation of a defecation count or the amount of defecation per unit time, and a prolonged situation of an excretion timing being a timing of an excretion behavior is preferably output as the detailed information. The decrease situation of a urine flow rate or the amount of urination indicates an increase situation of a urination interval in other words. The timing of an excretion behavior can be defined in such a way as to include at least an excretion date and time, and the other timing can also be defined in such a way as to include at least an occurrence date and time of a phenomenon being a target.

In this way, in the non-real time analysis, the detailed information can be output by identifying a feces characteristic, a feces color, and a urine color and calculating a feces amount and a urine amount from acquired imaging data. Further, in the non-real time analysis, information indicating whether a feces amount and a urine amount subjected to threshold processing exceed a predetermined threshold can be set as the detailed information or added to the detailed information. It is desirable that the detailed information output as a result of the threshold processing is transmitted (notified) to the terminal apparatus 50 directly or via the server 40. With such a notification (may include an alert), a carer can recognize a phenomenon needed to be handled.

Figure 8:
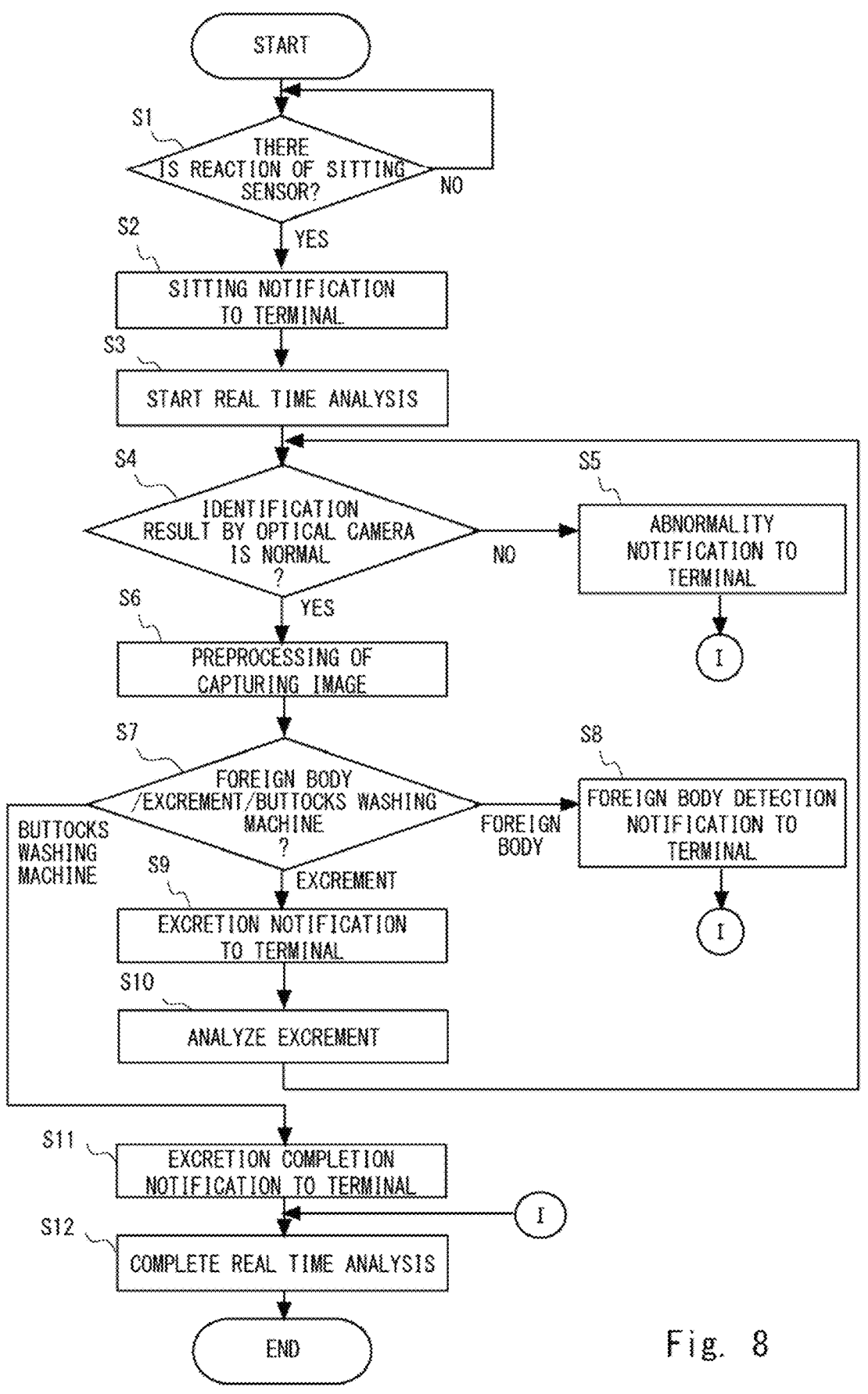
FIG. 8 is a flowchart for describing a processing example in the excrement analysis apparatus in the excrement analysis system in FIG. 2.

Next, one example of a procedure of real time analysis processing will be described with reference to FIG. 8. FIG. 8 is a flowchart for describing a processing example in the excrement analysis apparatus 10, and is a flowchart illustrating one example of an operation content of a real time analysis in which a user entering a toilet and sitting on a toilet seat is a trigger. The operation content described herein can be mainly performed by the CPU 11a while the CPU 11a mainly controls each unit.

First, whether there is a reaction of the range sensor 16a functioning as a sitting sensor is checked (step S1). When there is no reaction in step S1 (in the case of NO), a reaction of the sitting sensor is waited. When the user sits, the range sensor 16a reacts and YES is determined in step S1. When YES is determined in step S1, sitting is notified to the terminal apparatus 50 (step S2), and the real time analysis also starts (step S3). Note that, when the human detecting sensor 15a detects an entry before sitting, the entry can also be notified to the terminal apparatus 50, and the same also applies to an exit.

In the real time analysis, the first camera 16b performs capturing inside a toilet bowl, and whether the inside of the toilet bowl can be identified is determined (step S4). When an abnormality is detected (in the case of NO in step S4), an abnormality notification is transmitted to the terminal apparatus 50 of a carer (step S5). In this way, even when the inside of the toilet bowl cannot be normally captured, notification information indicating the failure is preferably transmitted to the terminal apparatus 50. On the other hand, when the inside of the toilet bowl can be normally identified (in the case of YES in step S4), the processing proceeds to a detailed analysis, and preprocessing of a capturing image is performed first (step S6).

After the preprocessing of the capturing image is performed in step S6, classification of a detection target object into any of a foreign body, excrement, and a buttocks washing machine is performed (step S7). When the foreign body is detected, a foreign body detection notification is made to the terminal apparatus 50 of the carer (step S8). When the excrement is detected, an excretion notification (transmission of notification information indicating excretion) is made to the terminal apparatus 50 of the carer (step S9), and an excrement analysis is also performed (step S10). By the excrement analysis, classification into any of feces, feces+urine, urine, and urine dripping is performed. After the processing in step S10, the processing returns to step S4.

When the detection target object detected in step S7 is the buttocks washing machine, excretion completion is determined, and an excretion completion notification (transmission of notification information indicating that excretion is completed) is made to the terminal apparatus 50 of the carer (step S11), and the real time analysis ends (step S12). Further, the excretion completion notification may be transmitted only after a point in time when there is no reaction of the sitting sensor. The reason is that the buttocks washing machine may be used for twice or more. Note that, the real time analysis also ends after step S5 and after step S8.

Figure 9:
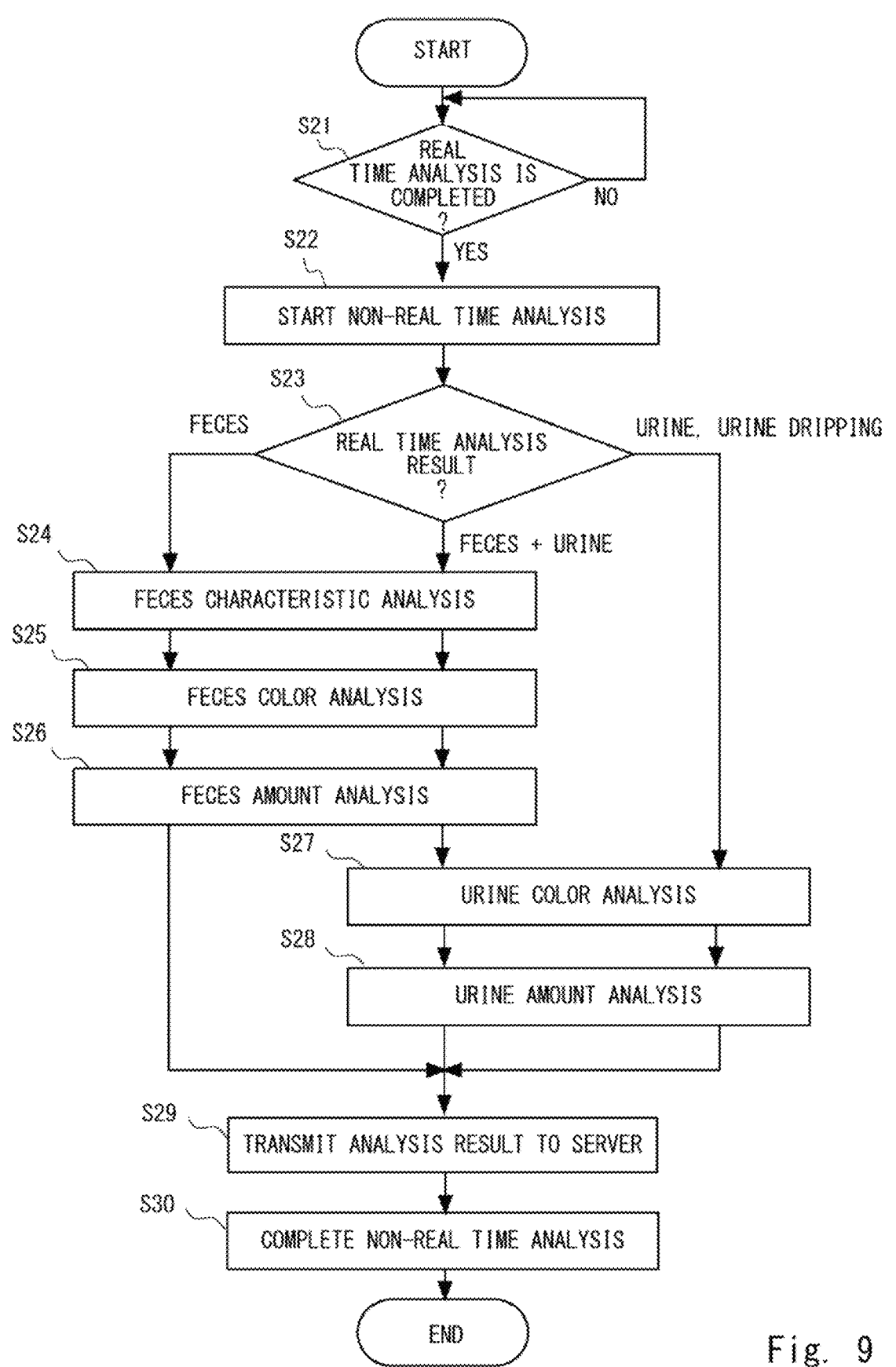
FIG. 9 is a flowchart for describing a processing example in the excrement analysis apparatus in the excrement analysis system in FIG. 2.

One example of a procedure of non-real time analysis processing will be described with reference to FIGS. 9 to 12. FIG. 9 is a flowchart for describing a processing example in the excrement analysis apparatus 10, and is a flowchart illustrating one example of an operation content of a non-real time analysis. The operation content described herein can be mainly performed by the CPU 11a while the CPU 11a mainly controls each unit. Further, FIGS. 10, 11, and 12 are diagrams respectively illustrating one example of a feces characteristic analysis, one example of a feces color analysis, one example of a urination amount analysis included in the non-real time analysis in the processing example in FIG. 9.

In the real time analysis exemplified in FIG. 8, while an analysis is performed by the space-saving, energy-saving CPU, a minimum necessary analysis to achieve a notification that requires immediacy to a carer is performed. In contrast, a more detailed analysis is performed on excrement in the non-real time analysis.

First, whether the real time analysis is completed is determined (step S21), and, when the real time analysis is completed (in the case of YES), the non-real time analysis starts (step S22). Alternatively, when a user identification function is provided, whether a predetermined excretion count is exceeded (or a predetermined period is passed) may be determined for each user, and the non-real time analysis may start when the predetermined excretion count is exceeded.

An input of the non-real time analysis and each analysis method are as described with reference to FIG. 7. First, a real time analysis result is determined (step S23), and a different analysis is performed depending on the result.

When the real time analysis result in step S23 is feces, a feces characteristic analysis (step S24), a feces color analysis (step S25), and a feces amount analysis (step S26) are performed. Of course, an order of the analyses is not limited. When the real time analysis result in step S23 is urine or urine dripping, a urine color analysis (step S27) and a urine amount analysis (step S28) are performed. Of course, an order of the analyses is not limited. When the real time analysis result in step S23 is feces+urine, the feces characteristic analysis (step S24), the feces color analysis (step S25), the feces amount analysis (step S26), the urine color analysis (step S27), and the urine amount analysis (step S28) are performed. Of course, an order of the analyses is not limited. Further, each of the analyses in steps S24 to S28 may be performed by, for example, using each individual learning model, but the plurality of analyses or all of the analyses may also be performed by using one learning model.

Herein, in the feces characteristic analysis in step S24, an analysis is performed by a comparison with a learned image by DL by using an image having a highest degree of reliability. The image having a highest degree of reliability may be an image itself indicated by imaging data, or an image acquired by performing preprocessing on imaging data by a preprocessing method suitable for an analysis of a feces characteristic. Further, in the feces characteristic analysis, for example, an analysis can be performed in conformity to a Bristol stool scale illustrated in FIG. 10. A result of the analysis can be classified into any of types 1 to 7 as illustrated in FIG. 10.

Further, in the feces color analysis in step S25, for example, preprocessing as illustrated in a processing procedure transitioning in an order of images 61, 62, and 63 in FIG. 11 can be performed. The preprocessing exemplified herein acquires the image 62 by removing a portion of a light color occupying a wide range from the original image 61, and then acquires the image 63 by removing a narrow region of the same color. Then, in the feces color analysis in step S25, an image like the image 63 in which necessary information is extracted (and/or added) by the preprocessing can be used, a range calculation between a color of the extracted feces and a feces reference color can be performed, and a color occupying a largest area in the extracted feces image can be set as a feces color. For example, feces-shaped objects of two colors are present in the image 63, and a color having a larger area can be set as a feces color. Note that, information added herein may also be, for example, information indicating an area, and the like.

In the feces amount analysis in step S26, a feces image (for example, the image 63, a real time analysis result, or the like) extracted by the preprocessing from an image at a point in time when excretion ends can be used, and a feces amount can be calculated (estimated) as an area ratio in a fixed size. However, even with the same area, a feces amount varies by a feces characteristic, and may thus be calculated by an area ratio associated with the feces characteristic and a reference value of the feces amount.

In the urine color analysis in step S27, the same method as that of the feces color analysis in step S25 is used, but a target image is a urine image instead of a feces image, a range calculation to a reference color can be performed, and a color occupying a largest area can be set as a urine color.

In the urine amount analysis in step S28, a urine amount can be calculated from all a urine dripping image classified into "urine dripping" as a real time analysis result by using information (urine dripping image information) such as time during which urine dripping continues, and a coefficient. Herein, for example, an average value of the amount of urination in general or of a user can be used as the coefficient described above. When all the urine dripping image described above is an image acquired in a fixed cycle, the amount of urination can be estimated from the image or an average of the amount of urination, and classification can be performed from the estimation result by determining which value a urine amount corresponds to. Note that, a value related to the amount of urination such as an average of the amount of urination can be acquired as a result of performing an investigation at all times, and is a variable parameter in this case.

Further, a result of the amount of urination can be classified into classes associated with a urine amount as exemplified in FIG. 12. In the example illustrated in FIG. 12, extremely small, small, medium, great, and especially great are class names, and are classified as less than a threshold a, equal to or more than the threshold a and less than a threshold b, equal to or more than the threshold b and less than a threshold c, equal to or more than the threshold c and less than a threshold d, and equal to or more than the threshold d, respectively.

When each of the analyses is completed, an analysis result is transmitted to the server 40 such as a cloud server (step S29). At this time, the analysis result being a transmission target can be both of a real time analysis result and a non-real time analysis result. Further, image data captured by the first camera 16b is not transmitted to the server 40. When transmission of the analysis result to the server 40 is completed in step S29, the non-real time analysis is also completed (step S30).

However, a procedure such as classification is not limited to that exemplified in FIGS. 8 to 12. The real time analysis may be performed by comparison processing with a learned image by DL as described above, but may be performed by first determining whether a target is excrement or a foreign body. The determination is performed in a fixed cycle, and, when the target is determined to be a foreign body, a foreign body notification to a carer is performed, and the processing proceeds to an excrement analysis that classifies the foreign body into five kinds of "feces", "feces+urine", "urine", "urine dripping", and "buttocks washing machine". Note that, the excrement analysis is also performed in a fixed cycle, and excretion completion is determined by detection of "buttocks washing machine". Upon the excretion completion, in the excrement analysis apparatus 10, an excretion completion notification is transmitted together with a real time analysis result to the terminal apparatus 50 of the carer, and the processing proceeds to a non-real time analysis using an image used in the real time analysis and the real time analysis result. All of the processing up to this point from sitting detection is performed in the excrement analysis apparatus 10 installed in a toilet bowl.

As described above, the excrement analysis apparatus 10 can acquire an excretion start, foreign body detection, excrement detection, and excretion completion as a real time analysis result, and can acquire a feces characteristic, a feces color, a urine amount, a urine color, and a urine amount as a non-real time analysis result. Both of the analysis results can be recorded in the server 40 on a cloud in a viewable state from the terminal apparatus 50, and can also be configured in such a way as to be transmitted to the terminal apparatus 50. Further, the server 40 accumulates the received analysis result, and performs a further analysis from the accumulated data, and the analysis result can also be configured in such a way as to be able to be notified to the terminal apparatus 50 or viewed from the terminal apparatus 50.

Further, the excrement analysis apparatus 10 or the present system including the excrement analysis apparatus 10 can be used in a private house on an assumption that a user is one person, but preferably has a function of identifying a user on an assumption that a plurality of users are present. The function is as described by using face image data acquired by the second camera 15b and identification data acquired by the Bluetooth module 14b. In this way, an entry notification, an exit notification, a sitting notification, a leaving notification, an excretion start notification, an excretion completion notification, and the like can be notified together with a user name to a carer, detailed information can be recorded for each user, and an excretion diary and a care record including the excretion diary can be generated.

Herein, a supplementary description of an excretion diary and a care record including the excretion diary is given. Information acquired by the real time analysis and the non-real time analysis can be used for generating an excretion diary and the like of a user by a carer. Further, a program of the terminal apparatus 50 may be executably incorporated in the terminal apparatus 50 as care software having a presentation function of presenting notification information received from the excrement analysis apparatus 10. Further, the care software may have a function of automatically inputting, to an excretion diary or a care record including the excretion diary, information transferred from the server 40 or information acquired when the server 40 is accessed. Further, such care software may be provided on the server 40, and, in that case, the care software may receive notification information and detailed information from the excrement analysis apparatus 10, and may automatically input the information in an excretion diary or a care record.

It is desirable that the excretion diary records a future excretion prediction. In order to achieve this, the present system has a prediction function. A prediction can be made from a result of the non-real time analysis (and a result of the real time analysis), and can be achieved by mounting, for example, a learned model that makes a prediction on at least one of the server 40 and the terminal apparatus 50. In the real time analysis and the non-real time analysis described above, an excretion date and time, the amount of excretion, and the like can be output for each user, and thus the present system can record an excretion diary in the end in the server 40 and/or the terminal apparatus 50. The present system may be configured in such a way as to use the excretion diary, input necessary information of the excretion diary to a learned model, and output a date and time (excretion timing), the amount, and the like of urination and defecation for a next or subsequent time. The output may be a tendency (such as an average interval) of urination and defecation. Alternatively, the prediction as described above may also be included in the non-real time analysis.

By providing such a prediction function, not only a burden of a daily excretion record, an excretion diary, and the like on a carer can be reduced, but also a tendency of the data and the like can be analyzed. In this way, when there is no record of defecation for a predetermined number of days, the present system can notify a user and a carer of an alert of constipation and encourage the user and the carer to handle the situation. For example, the present system predicts a urination time by checking a date and time of an excretion behavior and calculating an average interval time of the excretion behavior for each user, and, at a scheduled excretion time, the present system notifies a user and a carer of an excretion time, and thus reduces incontinence of the user and supports independence. Furthermore, a tendency of a urination disorder can be recognized from a urination interval exceeding a fixed threshold, and early consultation at a hospital can be achieved by notifying a user and a carer of an alarm from the present system. Further, the present system may be configured in such a way as to also similarly notify an alarm about a defecation interval. In this way, by checking information about a date and time of an excretion behavior and an excretion content and determining whether a set threshold is exceeded, the present system can recognize a urination disorder and a constipation tendency and notify a carer and a user of an alert. Then, the functions can reduce a burden on a carer and give considerate support to a user of a toilet.

Further, the present system also preferably has a function (a washing stopping function) of stopping clean water of a toilet in addition to a function of notifying a carer of an alarm when the excrement analysis apparatus 10 detects a foreign body other than excrement. In order to achieve this, the excrement analysis apparatus 10 may include a washing control unit (not illustrated) that controls a washing function of a toilet bowl. The washing control unit is connected or connectable to an apparatus (for example, a hot water washing toilet seat such as a washlet (registered trademark) having a function of flushing a toilet) having a washing function of a toilet bowl. Note that, a washing target of the hot water washing toilet seat described above is buttocks and the like of a user. The present system may also include such an apparatus or a toilet bowl integrated with a hot water washing toilet seat.

To give description with reference to the configuration example in FIG. 3, the CPU 11*a* and an interface (not illustrated) between the toilet seat 22 and the CPU 11*a* may be one example of the washing control unit. Note that, for the washing function, the amount of water flushing into the toilet bowl 20 may be controlled by using an existing technique (the toilet seat 22 may be controlled in this example). Then, when the CPU 11*a* notifies information including a foreign body as the notification information, the CPU 11*a* outputs a stop command for stopping the washing function to the toilet bowl side (the toilet seat 22 in this example), and thus the washing function is stopped. For example, the excrement analysis apparatus 10 notifies a remote-controllable power supply tap connected to a power cord of the toilet seat 22 of the toilet of power interruption, and stops the washing function of the toilet bowl 20 of the toilet. More specifically, it is possible to supply power to the toilet seat 22 via the Internet of things (IoT) tap, output a stop command to the IoT tap, and turn off the power. In this case, the stop command may be transmitted by, for example, the CPU 11*a* via the Bluetooth module 14*b*.

By providing such a washing stopping function, even when a user uses the washing function, since the washing function is stopped, the foreign body can be left without being flushed and then can be inspected as a sample and the like. Further, since the foreign body is not flushed and alert information indicating the detection of the foreign body is output, a carer of the user and the like can rush to the toilet, which can prevent the user from feeling the confusion caused by not flushing the foreign body.

As described above, the present system can achieve the effects described in the first example embodiment. Particularly or in addition to the effects, the present system has the following effects, for example.

The first effect is a point that, by automatically recording a content of excrement identified by a combination of the first camera and the machine learning, it is possible to eliminate the need for manual hearing about excrement, measurement of the amount of urination, confirmation of feces, and generation of an excretion diary, which has been carried out so far. In this way, it is possible to reduce the work time of a carer such as a caregiver.

The second effect is a point that a real time analysis allows an event (such as sitting, excretion, and foreign body detection) occurring in a toilet to be immediately notified to a carer, and the carer is released from a situation where the carer stays with a user during excretion.

The third effect is a point that, when a foreign body is detected in a real time analysis, an alert (alarm) is notified to a carer, thus it is possible to prevent an accident related to drainage of a toilet, and reduce a cost for handling drainage trouble.

The fourth effect is a point that, when an analysis of an image captured by the first camera 16*a* is performed, the excrement analysis apparatus 10 can perform all analysis processing and transmit only an analysis result to the server 40 such as a cloud server. In this way, imaging data about excrement are not seen by a third person, and a mental burden related to privacy of a user can be reduced.

The fifth effect is a point that, by dividing an analysis related to excrement into a real time analysis and a non-real time analysis, the CPU 11*a* built in the excrement analysis apparatus 10 can be space-saving and energy-saving, and the excrement analysis apparatus 10 is cheaper. The excrement analysis apparatus 10 is cheaper, and thus an introduction cost of a system also including a server and the like and a cost for maintenance in an event of a failure can be reduced.

The sixth effect is a point that a possibility of constipation or a urination disorder can be recognized from an excretion record in which an analysis result of excrement is recorded in a DB form and the like, thereby eliminating a need for administering a laxative that is unnecessary in consideration of safety but is performed due to reliability of hearing about presence or absence of feces, which has been carried out so far. In this way, a cost of medicine can be reduced.

The seventh effect is a point that a urination interval of a user can be individually recognized from an excretion record in which an analysis result of excrement is recorded in a DB form and the like. In this way, since the user does not need to use a diaper and a urine absorbing pad regularly, a cost can be reduced, and a carer can recognize a state of each user and easily support the independence of each user.

Third Example Embodiment

Figure 13:
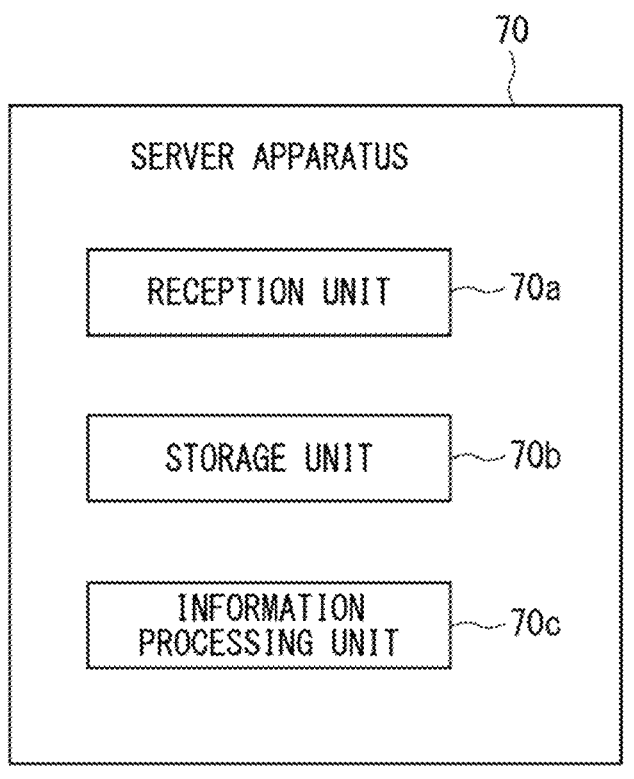
FIG. 13 is a block diagram illustrating one configuration example of a server apparatus according to a third example embodiment.

A third example embodiment will be mainly described with reference to FIGS. 13 to 13 while focusing on differences with the first and second example embodiments, but various examples described in the first and second example embodiments can be applied. FIG. 13 is a block diagram illustrating one configuration example of a server apparatus according to the third example embodiment.

As illustrated in FIG. 13, a server apparatus 70 according to the present example embodiment includes a reception unit 70*a* that receives detailed information from an excrement analysis apparatus 1 or an excrement analysis apparatus 10, a storage unit 70*b* that stores the detailed information received in the reception unit 70*a*, and an information processing unit 70*c*. The server apparatus 70 may be formed of a computer, and it can also be said that the information processing unit 70*c* is a control unit thereof.

In the present example embodiment, it is assumed that the detailed information described above includes at least information indicating an excretion date and time (occurrence date and time), a kind of excrement, and a shape of defecation. Then, the information processing unit 70*c* aggregates the detailed information for each shape of defecation. A simple example of the aggregate may include processing such as counting of a count for each shape or calculation of an average count for each fixed period, for example.

Further, the information processing unit 70*c* may extract, from the detailed information described above, information (information being an aggregate target) including an excretion date and time, a kind of excrement, and a shape of defecation, and may also aggregate the extracted information for each shape of defecation under various conditions.

In this way, the server apparatus 70 can aggregate accurate detailed information (may be referred to as excretion information) collected by the excrement analysis apparatus 1 or the excrement analysis apparatus 10. Further, for the aggregate processing, the aggregate processing of extracting necessary information from the detailed information and setting only the extracted information as a target can also be performed.

Further, an aggregated result can be stored in a storage apparatus such as the storage unit 70*b*. The aggregated result is preferably stored according to a request from an external apparatus in a state where the result can be provided to an external apparatus such as a terminal apparatus 50 used by a carer C and a terminal apparatus used by a user P of a toilet. In this case, the server apparatus 70 includes a provision unit (not illustrated) that provides a processing result in the information processing unit 70*c* to the external apparatus via a network and the like. The aggregated result is preferably stored in a database form, and is preferably stored in a server apparatus (for example, a cloud server apparatus) that can be accessed from the external apparatus. Note that, the aggregated result can be provided for various uses, and a method of the use and the like will be described in fourth and fifth example embodiments.

Further, the description is given on the assumption that the reception unit 70*a* receives the detailed information from the excrement analysis apparatus 1 or the excrement analysis apparatus 10. However, the detailed information may be information analyzed in an apparatus other than the excrement analysis apparatus 1 or the excrement analysis apparatus 10, and may be information received from an apparatus other than the excrement analysis apparatus 1 or the excrement analysis apparatus 10. The detailed information may be detailed information indicating a content of excretion being a result of analyzing excrement in a toilet bowl of a toilet from imaging data captured in the toilet bowl, and may include at least information indicating an excretion date and time, a kind of excrement, and a shape of defecation.

Fourth Example Embodiment

Figure 14:
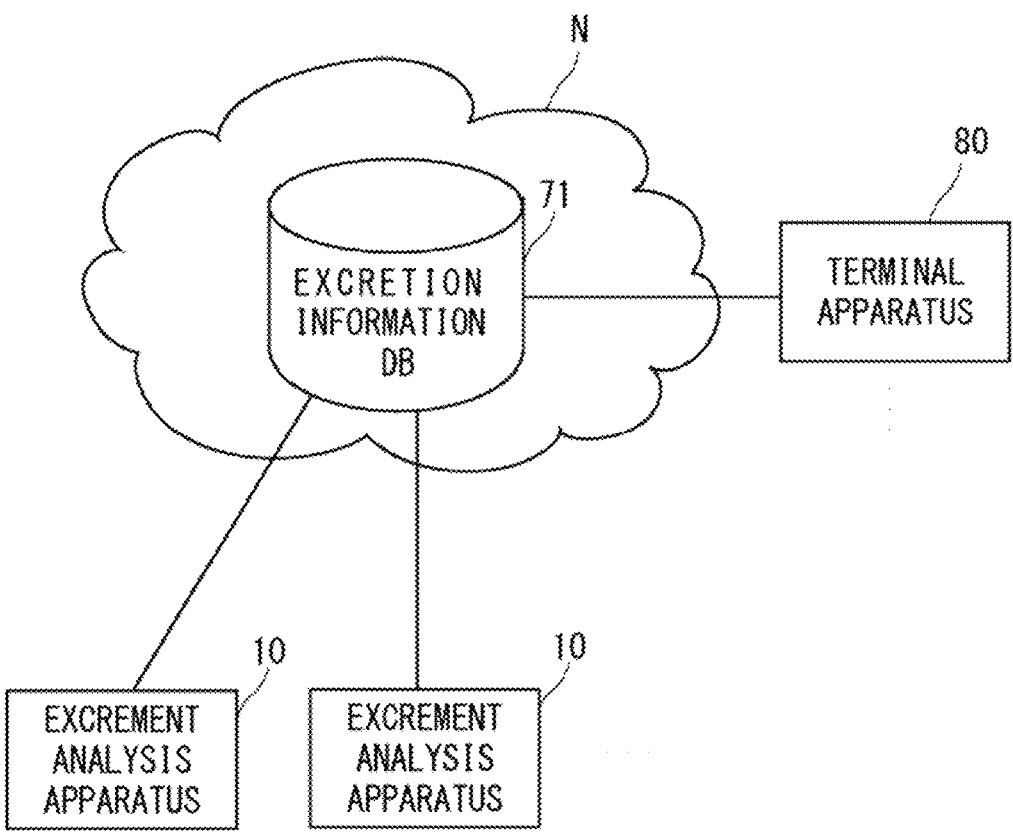
FIG. 14 is a diagram illustrating one configuration example of an analysis system according to a fourth example embodiment.

A fourth example embodiment will be mainly described with reference to FIGS. 14 to 20 while focusing on differences with the third example embodiment, but various examples described in the first to third example embodiments can be applied. FIG. 14 is a diagram illustrating one configuration example of an analysis system according to the fourth example embodiment, and FIG. 15 is a diagram illustrating one example of transmission information transmitted from an excrement analysis apparatus 10 in the analysis system in FIG. 14. FIG. 16 is a diagram illustrating one example of an intensive information table included in an excretion information database stored in a server apparatus in the analysis system in FIG. 14, and FIGS. 17 to 19 are diagrams illustrating an example of an aggregate information table included in the excretion information database.

As illustrated in FIG. 14, the analysis system according to the present example embodiment may be configured by connecting a plurality of the excrement analysis apparatuses 10 and a terminal apparatus 80 used by a toilet user or a supervisor such as a carer of the toilet user to a cloud network N including an excretion information database (DB) 71. The excretion information DB 71 may be stored in the storage unit 70*b* of the server apparatus 70 in FIG. 13.

In other words, in the analysis system, information included in the excretion information DB 71 is configured in such a way as to be providable to the terminal apparatus 80 on the cloud network N. The terminal apparatus 80 can acquire desired information (however, information according to a user of the terminal apparatus 80 in consideration of privacy) from the excretion information DB 71. The analysis system can provide a user of the terminal apparatus 80 with a service that provides such information. Note that, it can be said that constructing a DB on the cloud network N is beneficial in a point that a DB capacity, processing performance, and the number of apparatuses can also be flexibly changed according to the number of the excrement analysis apparatuses 10, the number of toilet users, and an actual usage situation.

A specific example of the excretion information DB 71 will be described with reference to FIGS. 15 to 19.

The excretion information DB 71 may include information (for example, an intensive information table 71*a* in FIG. 16) acquired by summarizing, in the information processing unit 70*c*, transmission information (for example, transmission information in FIG. 15) transmitted from the plurality of excrement analysis apparatuses 10, and may include information acquired by extracting information being an aggregate target from the information. Further, the excretion information DB 71 may include aggregated information (for example, aggregate information tables 71*b*, 71*c*, and 71*d* in FIGS. 17 to 19) as information provided on the network N.

The excrement analysis apparatus 10 collects excretion information (detailed information described above), and transmits the information (transmission information) together with user information and installation place information to the server apparatus 70 side. The excretion information to be collected may include the following information as exemplified in FIG. 15. In other words, the excretion information may include an excretion date and time (occurrence date and time), a kind of excrement (information indicating any of urination, defecation, and a foreign body), the amount of urination (for example, information indicating any of great, normal, and small), and a shape of defecation (for example, information indicating any of hard, normal, and diarrhea). Further, the excretion information may include a color of defecation, and may further include a count (a count of urination and defecation in one day).

As exemplified in FIG. 15, the transmission information may include such excretion information, user information including an age and a gender of a toilet user, and address information (installation place information) indicating an address of an installation place of a toilet or the toilet user. The user information and the address information are associated with the excretion information. The address information is preferably information in consideration of privacy, such as only a zip code. Note that, an installation place of a toilet may indicate an installation place of the excrement analysis apparatus 10. Further, in an example in which contact with the user is needed as described below, information such as a contact address of the user may be included in the user information. The transmission information may be received in the reception unit 70*a* of the server apparatus 70 in FIG. 13, and stored in the storage unit 70*b* as a target of extraction and aggregation in the information processing unit 70*c*.

The server apparatus 70 receives such transmission information, and registers the transmission information in the excretion information DB 71. For the registration, the intensive information table 71*a* (in a state where no information is stored) in FIG. 16 that registers the transmission information in the excretion information DB 71 on the cloud network N is generated in advance. The excrement analysis apparatus 10 collects the excretion information, and transmits the transmission information acquired by putting the excretion information with the user information and the installation place information as illustrated in FIG. 15 to the server apparatus 70 including the excretion information DB 71 on the cloud network N. When the excretion information DB 71 receives the transmission information transmitted from the excrement analysis apparatus 10, the excretion information DB 71 updates information stored in the intensive information table 71*a* with the transmission information.

Next, data aggregation in the excretion information DB 71 will be described. As described in the third example embodiment, the information processing unit 70*c* may extract, from the transmission information, information (information being an aggregate target) including an excretion date and time, a kind of excrement, and a shape of defecation, and may aggregate the extracted information for each shape of defecation under various conditions. The data aggregation can be performed from the intensive information table 71*a* on the excretion information DB 71, and is performed for generating provision information. Examples of a provision destination include a carer, a toilet user, and the like. The provision information is preferably information in which a content and a change of excretion are easy to view in a provision destination.

For example, aggregate information tables 71*b* to 71*d* illustrated in FIGS. 17 to 19 may be generated in advance in the excretion information DB 71. For generation of the tables, first, a view in which such an aggregate result can be acquired may be generated in advance, and information may be registered.

The aggregate information table 71*b* is a table indicating an aggregate result of a defecation shape, and can be generated by using the information about an occurrence date and time, a kind of excrement, and a shape of defecation from the intensive information table 71*a*. For example, information in which a kind of excrement is associated with defecation may be extracted from the intensive information table 71*a*, the extracted information may be classified into information about an occurrence date and time (occurrence month in this example) and information about a shape of defecation, and the classified information may be aggregated in the aggregate information table 71*b*. A tendency of the defecation shape can be viewed for each month from the aggregate information table 71*b*, and a person who views the information can recognize that the person is more likely to get out of condition in a month at frequent occurrence of diarrhea, for example.

The aggregate information table 71*c* is a table indicating an aggregate result of a defecation shape by age, and can be generated by using the information about an occurrence date and time, a kind of excrement, a shape of defecation, and an age from the intensive information table 71*a*. For example, information in which a kind of excrement is associated with defecation may be extracted from the intensive information table 71*a*, the extracted information may be classified into information about an occurrence date and time (occurrence month in this example), information about a shape of defecation, and information about an age, and the classified information may be aggregated in the aggregate information table 71*c*. A tendency of a defecation shape classified by age can be viewed for each month from the aggregate information table 71*c*.

The aggregate information table 71*d* is a table indicating an aggregate result of a defecation shape by region, and can be generated by using the information about an occurrence date and time, a kind of excrement, a shape of defecation, and an address (zip code) from the intensive information table 71*a*. For example, information in which a kind of excrement is associated with defecation may be extracted from the intensive information table 71*a*, the extracted information may be classified into information about an occurrence date and time (occurrence month in this example), information about a shape of defecation, and information about an address (zip code), and the classified information may be aggregated in the aggregate information table 71*d*. A tendency of a defecation shape classified by region can be viewed for each month from the aggregate information table 71*d*.

Further, as in the example in which a tendency can be recognized in the aggregate information tables 71*b* to 71*d*, the information processing unit 70*c* preferably analyzes a tendency of a time change in a shape of defecation. A technique for analyzing a tendency is not limited. Further, as an analysis result, for example, a sentence such as "month at frequent occurrence of diarrhea is ' '" may be provided for the aggregate information table 71*c*, for example.

Further, as exemplified in FIG. 15, the information indicating a color of defecation is preferably included in the detailed information in the transmission information. In that case, the information processing unit 70*c* preferably analyzes a tendency of a time change in a shape and a color of defecation. A result of analyzing a change tendency of a shape of defecation and a change tendency of a color can be used for a prediction of an infectious disease described below, and the like. For example, since a shape and a color of defecation change due to contraction of a disease in infectious gastroenteritis, an analysis result of a tendency of a change in defecation can be used for a prediction of such an infectious disease. Further, similarly, the information indicating the amount of defecation may be included in the detailed information in the transmission information.

Further, when an infectious disease is predicted, an occurrence situation of the infectious disease varies for each region, and thus a region also needs to be considered. When a region is considered, as described above, the reception unit 70*a* needs to receive the address information associated with the detailed information, and receives caution information that gives caution (including an alert) about spread of an infectious disease in order to predict the infectious disease.

The address information can be received together with the detailed information. The caution information can be received in a path different from that of the detailed information. For example, the caution information can be received by being read as input data from an operation unit included in the server apparatus 70 or from an external recording medium. Alternatively, the caution information can also be received by being regularly acquired by a server apparatus for providing caution information (for example, a server apparatus used for providing information by a health center) being connected to the server apparatus 70.

Then, the information processing unit 70*c* analyzes, from the address information and the detailed information, a tendency of a time change in defecation (such as a shape, or a shape and a color) for each region indicated by the address information, and predicts spread of the infectious disease described above for each region, based on an analysis result and the caution information (by combining the analysis result and the caution information). The address information and the detailed information used for an analysis may be information acquired by summarizing transmission information as exemplified in the intensive information table 71*a*, but is preferably an aggregate result as in the aggregate information table 71*d*. Further, the region may refer to a town unit of local governments, and may also be a jurisdictional district unit of a health center, a school district unit, and the like, and the address information that can distinguish a region being a prediction target may be received.

Further, a prediction method is not limited, and a prediction may be performed with the caution information, by determining whether a shape and a color that may be generated by an infectious disease increase in a defecation shape and a defecation color, and the like. Further, the reception unit 70*a* may receive environmental information including the caution information and weather information (prediction information about weather), and predict spread of an infectious disease for each region, based on a result of an analysis and the environmental information. Further, a prediction may be performed for each of a plurality of infectious diseases.

Then, the server apparatus 70 preferably includes a provision unit (not illustrated) that provides a predicted result for each region in the information processing unit 70*c* to a provision destination associated with each region. Since the prediction result is based on a result of defecation of a toilet user also including a sufferer without a diagnosis of contraction of a disease, it can be said that an actual infectious situation can be reflected more than the caution information. Further, the predicted result (the caution information about spread of the infectious disease) can be provided by making a notification from the server apparatus 70 to the terminal apparatus 80 such as a smartphone for each region such as an associated town unit of local governments and an associated school district unit.

In this way, the analysis system according to the present example embodiment can be constructed as an infectious disease prediction system for providing a spread prediction of an infectious disease and a prediction result of the infectious disease as information for maintaining health.

Further, a month unit is described as an example of an aggregate period of a defecation shape, but, for example, the aggregate period may be a day unit, a year unit, a unit of a predetermined number of months, a unit of a predetermined number of days, or a unit of a predetermined number of years. In this way, a tendency of a shape of defecation can be recognized for each day, each year, or the like. Further, for example, a result aggregated for each year may also be further aggregated for each day or each month.

Figure 20:
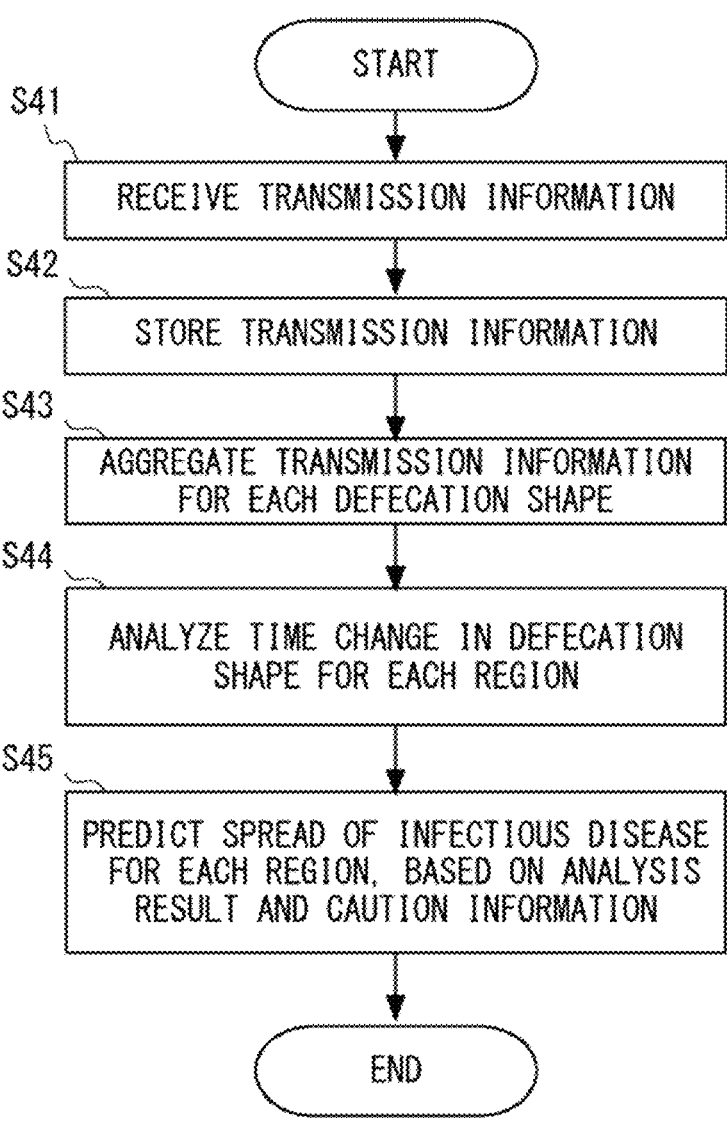
FIG. 20 is a flowchart for describing a processing example of the server apparatus in the analysis system in FIG. 14.

Next, a flow of processing of the server apparatus 70 in the infectious disease prediction system according to the present example embodiment will be schematically described with reference to FIG. 20. FIG. 20 is a flowchart for describing a processing example of the server apparatus 70.

First, the reception unit 70*a* of the server apparatus 70 receives transmission information (step S41), and stores the transmission information in the storage unit 70*b* (step S42). The information processing unit 70*c* aggregates the transmission information for each defecation shape, and stores an aggregate result in the storage unit 70*b* (step S43). In an example in which a prediction of an infectious disease is performed, the information processing unit 70*c* further analyzes a time change in deformation shape for each region (step S44). Next, the information processing unit 70*c* predicts spread of the infectious disease for each region, based on the analysis result and caution information about the infectious disease, and stores a prediction result in the storage unit 70*b* (step S45).

Next, effects related to a prediction of spread of an infectious disease will be particularly described.

First, a method of providing information about a current infectious disease and a problem thereof will be described.

Under present circumstances, when an infectious disease such as infectious gastroenteritis occurs, a medical institution reports the number of consulted patients with the infectious disease to a health center or the like, and the health center dispatches, as caution information (an advisory or an alert), information about spread of the infectious disease in a case where the reported number exceeds a reference. Thus, the health center knows the spread of the infectious disease in a jurisdictional district, but cannot recognize a place of a town of local governments and a school district where the infectious disease spreads since the health center does not recognize address information about the patients with the infectious disease. In this way, there is a contradiction that the infectious disease spreads in the jurisdictional district of the health center, but the infectious disease does not spread in a town unit of the local governments and a school district unit in the jurisdictional district. In order to solve the contradiction, the health center needs to dispatch an advisory and an alert in a town unit of the local governments and a school district unit, but the health center does not recognize address information about an individual patient with the infectious disease and cannot recognize a detailed spread range, and thus cannot solve the contradiction under present circumstances.

Further, a medical institution reports an aggregate of the number of patients with an infectious disease in a week to a health center on next Monday under present circumstances. The health center summarizes the report from the medical institution in a jurisdictional district, and dispatches an advisory and an alert when the number of the patients with the infectious disease exceeds a fixed number, and thus there is a time difference from an increase in the number of the patients with the infectious disease until the advisory and the alert are dispatched. In this way, since the medical institution reports a result aggregated in a week unit to the health center, there is a time difference from an increase in the number of the patients with the infectious disease until the advisory and the alert are dispatched.

In contrast, in the present example embodiment, excretion information collected by the excrement analysis apparatus 10 can be aggregated even in a unit of one day, for example. Thus, in the present example embodiment, an increase in a person whose defecation state is diarrhea can be recognized from a daily aggregate result, and a place of an associated town of local governments and an associated school district can be recognized from address information. Then, in the present example embodiment, by combining the information and information about occurrence of an infectious disease being dispatched from a health center, it is possible to predict spread of the infectious disease in the associated town of the local governments and the associated school district, and provide caution information for each region indicating a prediction result.

In this way, the infectious disease prediction system according to the present example embodiment collects information about a shape, a color, and the like of excrement, performs an analysis for each region, and predicts spread of an infectious disease by also using caution information about the infectious disease. Thus, according to the infectious disease prediction system, for example, even when caution information about spread of an infectious disease is dispatched with a jurisdictional district of a health center as a target, caution information in consideration of a more actual infectious situation can be provided in a town unit of local governments, a school district unit, and the like. Further, since caution information in consideration of a more actual infectious situation can be provided in the infectious disease prediction system, a problem that quick prevention of an infectious disease cannot be achieved due to a delay of caution information can be solved, and an effect of preventing expansion of the infectious disease can be expected.

Fifth Example Embodiment

Figure 21:
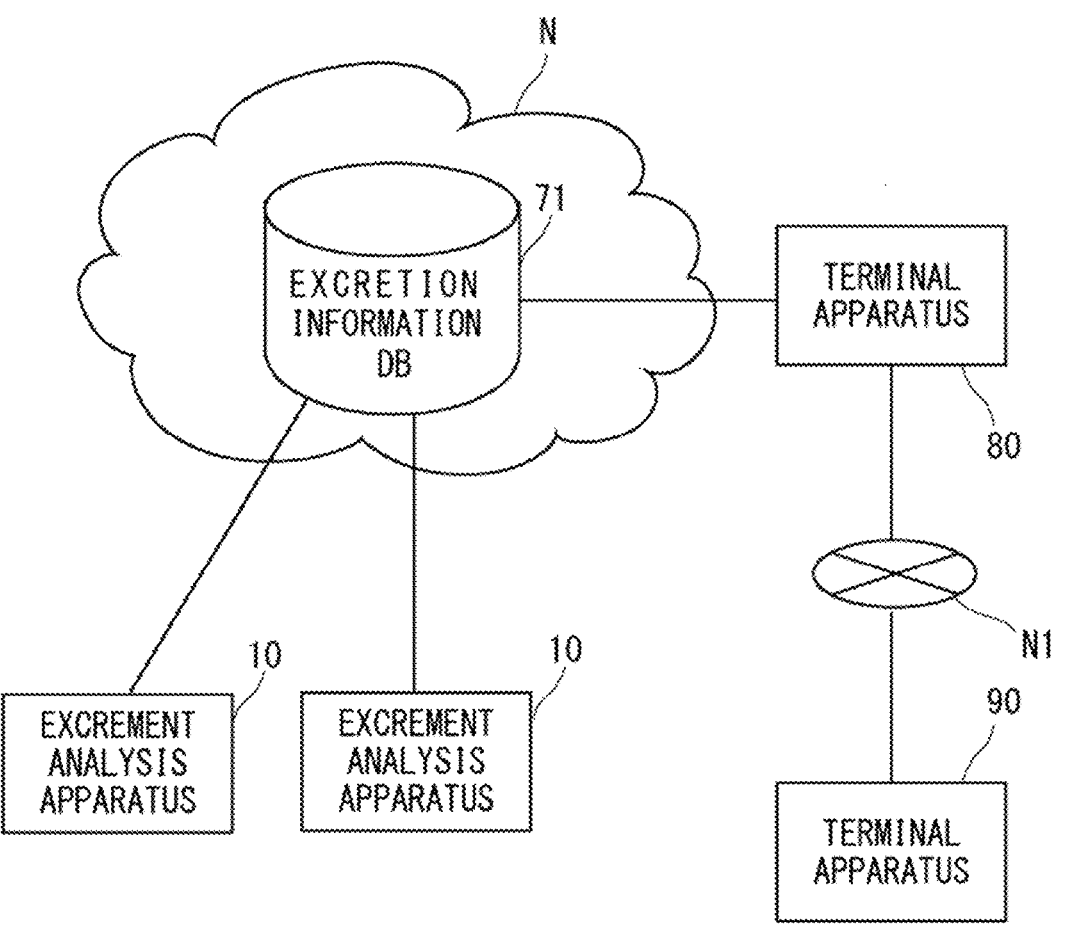
FIG. 21 is a diagram illustrating one configuration example of an analysis system according to a fifth example embodiment.

A fifth example embodiment will be mainly described with reference to FIGS. 21 to 24 while focusing on differences with the fourth example embodiment, but various examples described in the first to fourth example embodiments can be applied. FIG. 21 is a diagram illustrating one configuration example of an analysis system according to the fifth example embodiment, and FIGS. 22 and 23 are one example of an intensive information table and one example of an aggregate information table, respectively, included in an excretion information database stored in a server apparatus in the analysis system in FIG. 21.

As described in the fourth example embodiment, detailed information (excretion information) collected in an excrement analysis apparatus 10 can be used for preventing expansion of an infectious disease, but it is desirable to increase an advantage of installing the excrement analysis apparatus 10 that can be acquired by a toilet user himself/herself or a person who installs the excrement analysis apparatus 10. Then, points that the excretion information is subtlety information and there is a reluctance to provide the information also need to be considered.

Thus, in the present example embodiment, for a toilet user who provides information about defecation/urination through excretion, a person who installs the excrement analysis apparatus 10 can provide a service that predicts a health state from the information and a service that provides health advice suitable for a health state. In this way, an advantage of installing the excrement analysis apparatus 10 and providing information is generated, and, as a result, installation of the excrement analysis apparatus 10 can be promoted.

Such the present example embodiment will be specifically described.

In the analysis system according to the present example embodiment, the server apparatus 70 in FIG. 13 is configured in such a way as to perform the following processing. First, the reception unit 70a receives user information and address information associated with detailed information, and receives environmental information including weather information and infectious disease spread information indicating a result of spread of an infectious disease. The storage unit 70b stores the received information.

As illustrated in FIG. 21, the analysis system according to the present example embodiment may be configured by connecting a plurality of the excrement analysis apparatuses 10, a terminal apparatus 80 used by a supervisor such as a carer, and a terminal apparatus 90 used by a toilet user to a cloud network N including an excretion information DB 71. Herein, as illustrated, the terminal apparatus 90 may also be connected to the terminal apparatus 80 via a separate network N1 different from the cloud network N.

The information processing unit 70c analyzes, from the user information, the address information, the environmental information, and the detailed information, a tendency of a time change in defecation according to the environmental information for each user indicated by the user information. Then, the information processing unit 70c predicts, from a result of an analysis, a health state including a morbidity state of the infectious disease for each user indicated by the user information.

A method of an analysis and a prediction is not limited, but information may be aggregated for each user first in order to make it easy to be used for a health prediction for each user. More specifically, information for each user is extracted from the intensive information table 71a in FIG. 16 stored in the excretion information DB 71, and an individual-specific intensive information table 71e illustrated in FIG. 22 is generated. An analysis is performed by using information about an occurrence date and time, a kind of excrement, a shape of defecation, and a color of defecation from the individual-specific intensive information table 71e. For example, first, information in which a kind of excrement is associated with defecation is extracted from the individual-specific intensive information table 71e, the extracted information is classified into an occurrence date and time, a shape of defecation, and a color of defecation, and the classified information is aggregated in an aggregate information table 71f in FIG. 23. A tendency of a change in a shape and a color of defecation for each month can be viewed for the user from the aggregate information table 71f. Note that, a month unit is described as an example of an aggregate period of defecation, which is not limited thereto.

Further, as in the example in which a tendency can be recognized in the aggregate information table 71f, the information processing unit 70c performs an analysis of such a tendency. As described above, a technique for an analysis is not limited.

Then, the information processing unit 70c predicts a health state including a morbidity state of the infectious disease for each user from a result of analyzing the tendency of the defecation. Further, a prediction may be performed for each of a plurality of infectious diseases. As described above, a technique for a prediction is not limited, but detailed information for each user being accumulated so far may be analyzed, and a period in which each user is more likely to go out of condition may be predicted from the detailed information and environmental information or infection of an infectious disease of each user may be predicted from occurrence of the infectious disease in a neighboring region. Further, the information processing unit 70c can also generate, as health advice information for each user, information for preventing the user from going out of condition and a method of preventing infection with an infectious disease. The health advice information may be able to be provided in a format being prepared in advance according to a prediction result.

Further, the server apparatus 70 may include a provision unit (not illustrated) that provides a predicted result for each piece of user information in the information processing unit 70c to a contact address indicated by contact address information about a user indicated by each piece of the user information. Thus, the user information may include the contact address information indicating the contact address of the user of a toilet.

For example, a prediction result and health advice information may be configured in such a way as to be viewable by accessing a Web page from the terminal apparatus 90 such as a smartphone and specifying a user, or by logging in to an application program mounted on the terminal apparatus 90. A prediction result and health advice information may be stored in the storage unit 70b. Further, for a health prediction and health advice information, it is desirable that similar information is configured in such a way as to be viewable by not only a toilet user but also from a terminal apparatus used by a family living with the toilet user or a family living away from the toilet user.

Further, the present example embodiment may adopt not only a configuration in which the excrement analysis apparatuses 1 and 10 described in the first and second example embodiments acquire detailed information and the like, but also a configuration in which another apparatus acquires similar information. The similar information described above refers to detailed information indicating a content of excretion being a result of analyzing excrement in a toilet bowl of a toilet from imaging data captured in the toilet bowl, user information and address information associated with the detailed information, and environmental information. The environmental information may be information including weather information and infectious disease spread information indicating a result of spread of an infectious disease.

Figure 24:
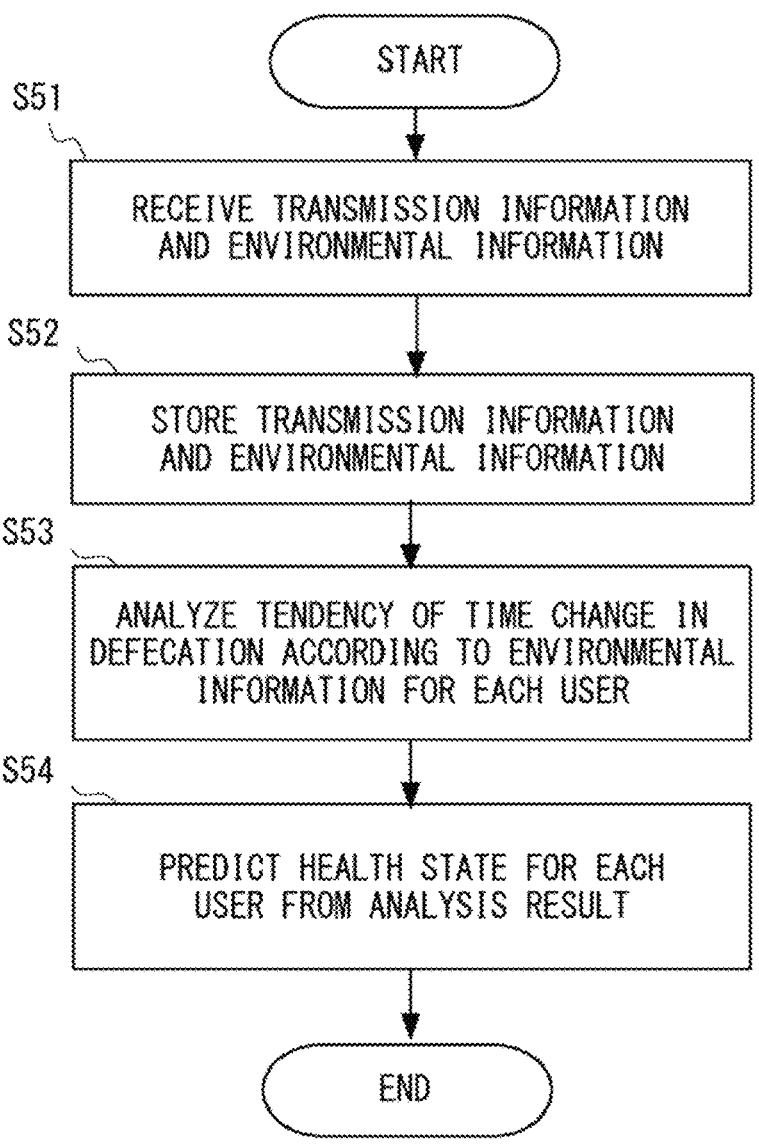
FIG. 24 is a flowchart for describing a processing example of the server apparatus in the analysis system in FIG. 21.

In this way, the analysis system according to the present example embodiment can be constructed as a health information provision system for predicting and providing an individual health state by using excretion information. Next, a flow of processing of the server apparatus 70 in the health information provision system according to the present example embodiment will be schematically described with reference to FIG. 24. FIG. 24 is a flowchart for describing a processing example of the server apparatus 70.

First, the reception unit 70a of the server apparatus 70 receives transmission information and environmental information (step S51), and stores the transmission information and the environmental information in the storage unit 70b (step S52). The information processing unit 70c analyzes, from user information, address information, the environmental information, and detailed information, a tendency of a time change in defecation according to the environmental information for each user indicated by the user information, and stores an analysis result in the storage unit 70b (step S53). Note that, prior to step S53, aggregation for each user may be performed in advance as described above. Furthermore, the information processing unit 70c predicts, from an analysis result, a health state including a morbidity state of an infectious disease for each user indicated by the user information, and stores a prediction result in the storage unit 70b (step S54).

According to the present example embodiment, since a health state of a user can be predicted from excretion information, and health information effective in promoting health can be provided to a user of the excrement analysis apparatus, an advantage of installing the excrement analysis apparatus can be generated, and an effect of progressing with installation of the excrement analysis apparatus can be expected.

Other Example Embodiment

[a]

In each example embodiment, the analysis system and a function of each apparatus included in the system have been described, but each apparatus is not limited to the illustrated configuration example and these functions may be implemented as each apparatus. For example, the server apparatus described above such as the server 40 and the server apparatus 70 may be constructed as a distributed system formed of a plurality of server apparatuses with distributed functions.

[b]

Figure 25:
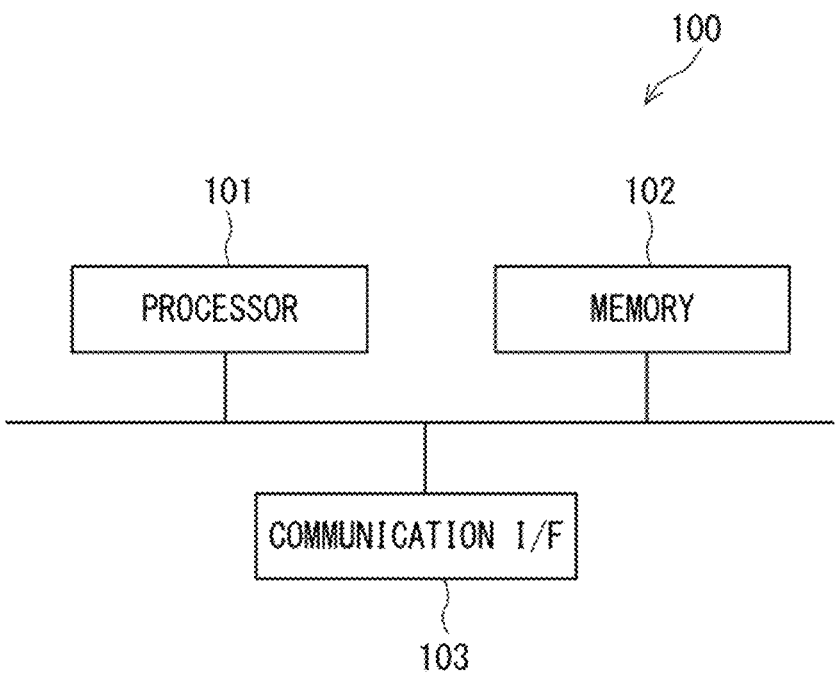
FIG. 25 is a diagram illustrating one example of a hardware configuration of the apparatus.

Each apparatus according to the first to fifth example embodiments may have the following hardware configuration. FIG. 25 is a diagram illustrating one example of a hardware configuration of the apparatus. The same also applies to the another example embodiment [a] described above.

A apparatus 100 illustrated in FIG. 25 may include a processor 101, a memory 102, and a communication interface (I/F) 103. The processor 101 may be, for example, a microprocessor, a microprocessor unit (MPU), a CPU, or the like. The processor 101 may also include a plurality of processors. The memory 102 is formed of a combination of a volatile memory and a nonvolatile memory. The functions of each apparatus described in the first to fifth example embodiments are implemented by the processor 101 that reads and executes the program stored in the memory 102. At this time, transmission/reception of information with another apparatus may be performed via the communication I/F 103 or an input/output interface (not illustrated). Particularly, when the apparatus 100 is an excrement analysis apparatus, transmission/reception of information (including imaging data) of an image capture apparatus built in or externally attached to the apparatus 100 can also be performed via the communication I/F 103 or the input/output interface (not illustrated).

In the example described above, the program may be stored by using various types of non-transitory computer-readable mediums, and may be supplied to a computer. The non-transitory computer-readable medium includes various types of tangible storage mediums. Examples of the non-transitory computer-readable medium include a magnetic recording medium (for example, a flexible disk, a magnetic tape, a hard disk drive), and a magneto-optical recording medium (for example, a magneto-optical disk). Moreover, this example includes a CD-ROM (Read Only Memory), a CD-R, and a CD-R/W. Moreover, this example includes a semiconductor memory (for example, a mask ROM, a programmable ROM (PROM), an erasable PROM (EPROM), a flash ROM, a random access memory (RAM)). Further, the program may also be supplied to the computer by various types of transitory computer-readable mediums. Examples of the transitory computer-readable medium include an electrical signal, an optical signal, and an electromagnetic wave. The transitory computer-readable medium may supply the program to the computer via a wired communication path such as an electric wire and an optical fiber or a wireless communication path.

[c]

Moreover, in the first and second example embodiments described above, as illustrated by exemplifying the procedure of an excrement analysis method in the excrement analysis system, the present disclosure may also take the form of the excrement analysis method (analysis method). The excrement analysis method may include the following input step, holding step, first analysis step, and second analysis step. In the input step, an excrement analysis apparatus inputs imaging data captured by an image capture apparatus installed in such a way as to include, in a capturing range, an excretion range of excrement in a toilet bowl of a toilet. In the holding step, the excrement analysis apparatus temporarily holds the imaging data input in the input step. In the first analysis step, the excrement analysis apparatus analyzes first analysis target data being the imaging data input in the input step, and outputs notification information to an observer who observes a user of the toilet. In the second analysis step, the excrement analysis apparatus analyzes second analysis target data being the imaging data input in the input step and temporarily held in the holding step, and outputs detailed information indicating a content of excretion. Note that, other examples are as described in the first and second example embodiments. Further, it can be said that the program is a program for causing the excrement analysis apparatus (computer for control included in the excrement analysis apparatus) to perform the input step, the holding step, the first analysis step, and the second analysis step.

Moreover, in the third and fourth example embodiments, as illustrated by exemplifying the procedure of an analysis method in the analysis system, the present disclosure may also take the form of another analysis method. The analysis method herein includes the following reception step, storage step, and information processing step, and preferably includes the following provision step. In the reception step, a server apparatus receives detailed information (also referred to as excretion information) indicating a content of excretion being a result of analyzing excrement in a toilet bowl of a toilet from imaging data captured in the toilet bowl. In the storage step, the server apparatus stores the detailed information received in the reception step. Herein, the detailed information includes at least information indicating an excretion date and time, a kind of excrement, and a shape of defecation. In the information processing step, the server apparatus aggregates the detailed information for each shape of the defecation. In the provision step, the server apparatus provides a processing result in the information processing step to an external apparatus. Note that, other examples are as described in the third to fifth example embodiments. Further, in this case, it can be said that the program is a program for causing the server apparatus (computer) to perform the reception step, the storage step, and the information processing step (and preferably the provision step in addition to the reception step, the storage step, and the information processing step).

Moreover, in the fifth example embodiment, as illustrated by exemplifying the procedure of an analysis method in the analysis system, the present disclosure may also take the form of another analysis method. The analysis method herein includes the following reception step, storage step, and information processing step, and preferably includes the following provision step. In the reception step, a server apparatus receives detailed information indicating a content of excretion being a result of analyzing excrement in a toilet bowl of a toilet from imaging data captured in the toilet bowl, user information and address information associated with the detailed information, and environmental information. Herein, the detailed information includes at least information indicating an excretion date and time, a kind of excrement, and a shape of defecation. Further, the user information is information indicating a user of the toilet, and the address information is information indicating an address where a user of the toilet lives or an address of an installation place of the toilet. Further, the environmental information is information including weather information and infectious disease spread information indicating a result of spread of an infectious disease. In the storage step, the server apparatus stores the detailed information, the user information, the address information, and the environmental information received in the reception step. In the information processing step, the server apparatus analyzes, from the user information, the address information, the environmental information, and the detailed information, a tendency of a time change in the defecation according to the environmental information for each user indicated by the user information. In the information processing step, the server apparatus further predicts, from a result of an analysis, a health state including a morbidity state of the infectious disease for each user indicated by the user information. In the provision step, the server apparatus provides a processing result in the information processing step to an external apparatus (contact address of the user). Note that, other examples are as described in the fifth example embodiment. Further, in this case, it can be said that the program is a program for causing the server apparatus (computer) to perform the reception step, the storage step, and the information processing step (and preferably the provision step in addition to the reception step, the storage step, and the information processing step).

Note that the present disclosure is not limited to the example embodiments described above, and may be appropriately modified without departing from the scope of the present disclosure. Further, the present disclosure may be implemented by appropriately combining the example embodiments.

A part or the whole of the above-described example embodiments may also be described as in supplementary notes below, which is not limited thereto.

<Supplementary Notes>

(Supplementary note 1)

1. An excrement analysis apparatus comprising:
an input unit that inputs imaging data captured by an image capture apparatus installed in such a way as to include, in a capturing range, an excretion range of excrement in a toilet bowl of a toilet;
a holding unit that temporarily holds imaging data input by the input unit;
a first analysis unit that analyzes first analysis target data being imaging data input by the input unit, and outputs notification information to an observer who observes a user of the toilet; and
a second analysis unit that analyzes second analysis target data being imaging data that is input by the input unit and temporarily held by the holding unit, and outputs detailed information indicating a content of excretion.

(Supplementary note 2)

The excrement analysis apparatus according to supplementary note 1, wherein the first analysis unit performs an analysis of whether a foreign body being an object other than feces and urine is included as a subject except for the toilet bowl and washing liquid for the toilet bowl, and outputs, as at least a part of the notification information, foreign body information indicating whether a foreign body is included.

(Supplementary note 3)

The excrement analysis apparatus according to supplementary note 1 or 2, wherein the first analysis unit outputs the notification information by transmitting the notification information to a terminal apparatus to be used by the observer.

(Supplementary note 4)

The excrement analysis apparatus according to any one of supplementary notes 1 to 3, wherein the second analysis unit outputs the detailed information by transmitting the detailed information to a server apparatus connected to the excrement analysis apparatus via a network.

(Supplementary note 5)

The excrement analysis apparatus according to supplementary note 4, wherein the first analysis unit outputs the notification information by transmitting the notification information to the server apparatus.

(Supplementary note 6)

The excrement analysis apparatus according to any one of supplementary notes 1 to 5, wherein the holding unit temporarily holds an analysis result by the first analysis unit as a part of the second analysis target data.

(Supplementary note 7)

The excrement analysis apparatus according to any one of supplementary notes 1 to 6, wherein the first analysis unit acquires the notification information from the first analysis target data by using a learned model of inputting the first analysis target data and outputting the notification information.

(Supplementary note 8)

The excrement analysis apparatus according to any one of supplementary notes 1 to 7, wherein the second analysis unit acquires at least a part of the detailed information from the second analysis target data by using a learned model of inputting the second analysis target data and outputting the detailed information.

(Supplementary note 9)

The excrement analysis apparatus according to any one of supplementary notes 1 to 8, wherein the second analysis unit acquires at least a part of the detailed information by performing image processing on the second analysis target data.

(Supplementary note 10)

The excrement analysis apparatus according to any one of supplementary notes 1 to 9, wherein the second analysis unit outputs, as the detailed information, information about at least one of a urine flow rate or an amount of urination, a defecation count or an amount of defecation per unit time, and an excretion timing being a timing of an excretion behavior.

(Supplementary note 11)

The excrement analysis apparatus according to supplementary note 10, wherein the second analysis unit outputs, as the detailed information, information indicating at least one of a decrease situation of a urine flow rate or an amount of urination, a decrease situation of a defecation count or an amount of defecation per unit time, and a prolonged situation of an excretion timing being a timing of an excretion behavior.

(Supplementary note 12)

The excrement analysis apparatus according to any one of supplementary notes 1 to 11, wherein the first analysis unit outputs, as at least a part of the notification information, at least one of information indicating a usage situation of a buttocks washing machine installed in the toilet bowl and information indicating that sitting is performed on the toilet bowl.

(Supplementary note 13)

The excrement analysis apparatus according to any one of supplementary notes 1 to 12, further comprising the image capture apparatus.

(Supplementary note 14)

An analysis system comprising:

the excrement analysis apparatus according to any one of supplementary notes 1 to 13; a terminal apparatus being connected to the excrement analysis apparatus and used by the observer; and a server apparatus being connected to the excrement analysis apparatus and the terminal apparatus, wherein the excrement analysis apparatus outputs the notification information by transmitting the notification information to the terminal apparatus, and outputs the detailed information by transmitting the detailed information to the server apparatus, the server apparatus stores the detailed information received from the excrement analysis apparatus in a viewable state from the terminal apparatus, and the terminal apparatus includes a diary generation unit that generates an excretion diary, based on the notification information received from the excrement analysis apparatus and the detailed information stored in the server apparatus.

(Supplementary note 15)

A server apparatus comprising:

a reception unit that receives the detailed information from the excrement analysis apparatus according to any one of supplementary notes 1 to 13;

a storage unit that stores the detailed information received by the reception unit; and an information processing unit, wherein the detailed information includes at least information indicating an excretion date and time, a kind of excrement, and a shape of defecation, and the information processing unit aggregates the detailed information for each shape of the defecation.

(Supplementary note 16)

A server apparatus comprising:

a reception unit that receives detailed information indicating a content of excretion being a result of analyzing excrement in a toilet bowl of a toilet from imaging data captured in the toilet bowl;

a storage unit that stores the detailed information received by the reception unit; and an information processing unit, wherein the detailed information includes at least information indicating an excretion date and time, a kind of excrement, and a shape of defecation, and the information processing unit aggregates the detailed information for each shape of the defecation.

(Supplementary note 17)

The server apparatus according to supplementary note 15 or 16, wherein the information processing unit analyzes a tendency of a time change in the shape of the defecation.

(Supplementary note 18)

The server apparatus according to supplementary note 15 or 16, wherein the detailed information includes information indicating a color of the defecation, and the information processing unit analyzes a tendency of a time change in the shape and the color of the defecation.

(Supplementary note 19)

The server apparatus according to any one of supplementary notes 15 to 18, further comprising a provision unit that provides a processing result by the information processing unit to an external apparatus.

(Supplementary note 20)

The server apparatus according to any one of supplementary notes 17 to 19, wherein the reception unit receives address information that is associated with the detailed information and indicates an address where a user of the toilet lives or an address of an installation place of the toilet, and receives caution information that gives caution about spread of an infectious disease, and the information processing unit analyzes, from the address information and the detailed information, a tendency of a time change in the defecation for each region indicated by the address information, and predicts spread of the infectious disease for the each region, based on a result of an analysis and the caution information.

(Supplementary note 21)

The server apparatus according to supplementary note 20, further comprising a provision unit that provides a predicted result for the each region by the information processing unit to a provision destination associated with each region.

(Supplementary note 22)

The server apparatus according to any one of supplementary notes 17 to 19, wherein the reception unit receives user information that is associated with the detailed information and indicates a user of the toilet and address information that is associated with the detailed information and indicates an address where a user of the toilet lives or an address of an installation place of the toilet, and receives environmental information including weather information and infectious disease spread information indicating a result of spread of an infectious disease, and the information processing unit analyzes, from the user information, the address information, the environmental information, and the detailed information, a tendency of a time change in the defecation according to the environmental information for each user indicated by the user information, and predicts, from a result of an analysis, a health state including a morbidity state of the infectious disease for each user indicated by the user information.

(Supplementary note 23)

A server apparatus comprising:

a reception unit that receives detailed information indicating a content of excretion being a result of analyzing excrement in a toilet bowl of a toilet from imaging data captured in the toilet bowl, user information that is associated with the detailed information and indicates a user of the toilet, address information that is associated with the detailed information and indicates an address where a user of the toilet lives or an address of an installation place of the toilet, and environmental information including weather information and infectious disease spread information indicating a result of spread of an infectious disease;

a storage unit that stores the detailed information, the user information, the address information, and the environmental information that are received by the reception unit; and an information processing unit, wherein the detailed information includes at least information indicating an excretion date and time, a kind of excrement, and a shape of defecation, and the information processing unit analyzes, from the user information, the address information, the environmental information, and the detailed information, a tendency of a time change in the defecation according to the environmental information for each user indicated by the user information, and predicts, from a result of an analysis, a health state including a morbidity state of the infectious disease for each user indicated by the user information.

(Supplementary note 24)

The server apparatus according to supplementary note 22 or 23, wherein the user information includes contact address information indicating a contact address of a user of the toilet, and the server apparatus further comprises a provision unit that provides a predicted result for each piece of the user information by the information processing unit to a contact address indicated by the contact address information for a user indicated by each piece of user information.

(Supplementary note 25)

An analysis method comprising:

an input step of, by an excrement analysis apparatus, inputting imaging data captured by an image capture apparatus installed in such a way as to include, in a capturing range, an excretion range of excrement in a toilet bowl of a toilet;

a holding step of, by the excrement analysis apparatus, temporarily holding imaging data input in the input step;

a first analysis step of, by the excrement analysis apparatus, analyzing first analysis target data being imaging data input in the input step, and outputting notification information to an observer who observes a user of the toilet; and a second analysis step of, by the excrement analysis apparatus, analyzing second analysis target data being imaging data that is input in the input step and temporarily held in the holding step, and outputting detailed information indicating a content of excretion.

(Supplementary note 26)

An analysis method according to supplementary note 25, further comprising:

a reception step of, by a server apparatus, receiving the detailed information;

a storage step of, by the server apparatus, storing the detailed information received in the reception step;

an information processing step; and a provision step, wherein the detailed information includes at least information indicating an excretion date and time, a kind of excrement, and a shape of defecation, the information processing step includes, by the server apparatus, aggregating the detailed information for each shape of the defecation, and the provision step includes, by the server apparatus, providing a processing result in the information processing step to an external apparatus.

(Supplementary note 27)

An analysis method comprising:

a reception step of, by a server apparatus, receiving detailed information indicating a content of excretion being a result of analyzing excrement in a toilet bowl of a toilet from imaging data captured in the toilet bowl;

a storage step of, by the server apparatus, storing the detailed information received in the reception step;

an information processing step; and a provision step, wherein the detailed information includes at least information indicating an excretion date and time, a kind of excrement, and a shape of defecation, the information processing step includes, by the server apparatus, aggregating the detailed information for each shape of the defecation, and the provision step includes, by the server apparatus, providing a processing result in the information processing step to an external apparatus.

(Supplementary note 28)

A program for causing a computer for control included in an excrement analysis apparatus to perform:

an input step of inputting imaging data captured by an image capture apparatus installed in such a way as to include, in a capturing range, an excretion range of excrement in a toilet bowl of a toilet;

a holding step of temporarily holding imaging data input in the input step;

a first analysis step of analyzing first analysis target data being imaging data input in the input step, and outputting notification information to an observer who observes a user of the toilet; and a second analysis step of analyzing second analysis target data being imaging data that is input in the input step and temporarily held in the holding step, and outputting detailed information indicating a content of excretion.

(Supplementary note 29)

The program according to supplementary note 28, wherein the program is a program for causing the computer to perform:

a reception step of receiving, as the detailed information, detailed information including at least information indicating an excretion date and time, a kind of excrement, and a shape of defecation;

a storage step of storing the detailed information received in the reception step;

an information processing step of aggregating the detailed information for each shape of the defecation; and a provision step of providing a processing result in the information processing step to an external apparatus.

(Supplementary note 30)

A program for causing a computer to perform:

a reception step of receiving detailed information that indicates a content of excretion being a result of analyzing excrement in a toilet bowl of a toilet from imaging data captured in the toilet bowl, and includes at least information indicating an excretion date and time, a kind of excrement, and a shape of defecation;

a storage step of storing the detailed information received in the reception step;

an information processing step of aggregating the detailed information for each shape of the defecation; and a provision step of providing a processing result in the information processing step to an external apparatus.

Although the invention of the present application has been described with reference to the example embodiments, the invention of the present application is not limited to the above-described example embodiments. Various modifications that can be understood by those skilled in the art can be made to the configuration and the details of the invention of the present application within the scope of the invention.

This application is based upon and claims the benefit of priority from Japanese patent application No. 2020-097575, filed on Jun. 4, 2020 and Japanese patent application No. 2020-179605, filed on Oct. 27, 2020, the disclosure of which is incorporated herein in its entirety by reference.

REFERENCE SIGNS LIST 1, 10 EXCREMENT ANALYSIS APPARATUS
1a INPUT UNIT
1b HOLDING UNIT
1c FIRST ANALYSIS UNIT
1d SECOND ANALYSIS UNIT
11 SECOND EXTERNAL BOX
11a CPU
11b CONNECTOR
11d, 11d USB I/F
12 INTER-BOX CONNECTION UNIT
13 FIRST EXTERNAL BOX
14a WiFi MODULE
14b Bluetooth MODULE
15a HUMAN DETECTING SENSOR
15b SECOND CAMERA
16a RANGE SENSOR
16b FIRST CAMERA
20 TOILET BOWL
21 MAIN BODY
22 TOILET SEAT
23 TOILET SEAT COVER
30 TOILET BOWL WITH EXCREMENT ANALYSIS APPARATUS
40 SERVER
41 CONTROL UNIT
42 STORAGE UNIT
50, 80, 90 TERMINAL APPARATUS
70 SERVER APPARATUS
70a RECEPTION UNIT
70b STORAGE UNIT
70c INFORMATION PROCESSING UNIT
100 APPARATUS
101 PROCESSOR
102 MEMORY
103 COMMUNICATION INTERFACE

What is claimed is:

1. An excrement analysis apparatus comprising:

an inputter configured to input imaging data captured by an image capture apparatus installed in such a way as to include, in a capturing range, an excretion range of excrement in a toilet bowl of a toilet:

a first analyzer configured to analyze first analysis target data being imaging data input by the inputter as a real time analysis, and output notification information to an observer who observes a user of the toilet:

a memory configured to temporarily hold the imaging data input by the inputter; and a second analyzer configured to analyze second analysis target data being the imaging data that is temporarily held by the memory as a non-real time analysis, and output detailed information indicating a content of excretion, wherein the first analyzer performs an analysis to determine whether a foreign body is present in the first analysis target data, the foreign body being an object other than feces and urine and a subject except for the toilet bowl and washing liquid for the toilet bowl; and in response to determining that the foreign body is present, the first analyzer:

outputs, as the notification information, an alert requiring rushing action by the observer in case of emergency.

2. The excrement analysis apparatus according to claim 1, wherein the first analyzer outputs the notification information by transmitting the notification information to a terminal apparatus to be used by the observer.

3. The excrement analysis apparatus according to claim 1, wherein the second analyzer outputs the detailed information by transmitting the detailed information to a server apparatus connected to the excrement analysis apparatus via a network.

4. The excrement analysis apparatus according to claim 3, wherein the first analyzer outputs the notification information by transmitting the notification information to the server apparatus.

5. The excrement analysis apparatus according to claim 1, wherein the memory temporarily holds an analysis result by the first analyzer as a part of the second analysis target data.

6. The excrement analysis apparatus according to claim 1, wherein the first analyzer acquires the notification information from the first analysis target data by using a learned model of inputting the first analysis target data and outputting the notification information.

7. The excrement analysis apparatus according to claim 1, wherein the second analyzer acquires at least a part of the detailed information from the second analysis target data by using a learned model of inputting the second analysis target data and outputting the detailed information.

8. The excrement analysis apparatus according to claim 1, wherein the first analyzer outputs, as at least a part of the notification information, at least one of information indicating a usage situation of a buttocks washing machine installed in the toilet bowl and information indicating that sitting is performed on the toilet bowl.

9. The excrement analysis apparatus according to claim 1, further comprising the image capture apparatus.

10. An analysis system comprising:
the excrement analysis apparatus according to claim 1; a terminal apparatus being connected to the excrement analysis apparatus and used by the observer; and a server apparatus being connected to the excrement analysis apparatus and the terminal apparatus, wherein
the excrement analysis apparatus outputs the notification information by transmitting the notification information to the terminal apparatus, and outputs the detailed information by transmitting the detailed information to the server apparatus,
the server apparatus stores the detailed information received from the excrement analysis apparatus in a viewable state from the terminal apparatus, and
the terminal apparatus includes a diary generator configured to generate an excretion diary, based on the notification information received from the excrement analysis apparatus and the detailed information stored in the server apparatus.

11. The excrement analysis apparatus according to claim 1, wherein the foreign body is at least one of vomit, blood vomiting, a urine absorbing pad, a diaper and a toilet paper core.

12. The excrement analysis apparatus according to claim 1, wherein the notification information to the observer does not contain the imaging data captured by the image capture apparatus.

13. The excrement analysis apparatus according to claim 1, wherein the second analyzer analyzes the imaging data to determine at least one of a feces characteristic, a feces color, a feces amount, a urine color, and a urine amount.

14. The excrement analysis apparatus according to claim 1, wherein the second analyzer analyzes the imaging data to acquire a comparison result by comparing a feces amount and a urine amount from a predetermined threshold, and outputs the detailed information containing the comparison result.

15. The excrement analysis apparatus according to claim 13, wherein the memory temporarily holds the imaging data input by the inputter; and
the detailed information does not contain the imaging data captured by the image capture apparatus.

16. The excrement analysis apparatus according to claim 1,
wherein the detailed information:

does not include the imaging data captured by the image capture apparatus; and
comprises information indicating at least one selected from the group consisting of a feces characteristic, a feces amount, a feces color, a urine amount, a urine color, a defecation count or an amount of defecation per unit time, and an excretion timing.

17. The excrement analysis apparatus according to claim 1,
wherein the alert requires immediate action by the observer to remove the object.

18. An analysis method comprising:
by an excrement analysis apparatus, inputting imaging data captured by an image capture apparatus installed in such a way as to include, in a capturing range, an excretion range of excrement in a toilet bowl of a toilet;
by the excrement analysis apparatus, analyzing first analysis target data being imaging data input in the inputting as a real time analysis, and outputting notification information to an observer who observes a user of the toilet;
by the excrement analysis apparatus, temporarily holding imaging data input in the inputting, and
by the excrement analysis apparatus, analyzing second analysis target data being imaging data that is temporarily held in the temporarily holding as a non-real time analysis, and outputting detailed information indicating a content of excretion,
wherein the first analyzer performs an analysis to determine whether a foreign body is present in the first analysis target data, the foreign body being an object other than feces and urine and a subject except for the toilet bowl and washing liquid for the toilet bowl; and
in response to determining that the foreign body is present, the first analyzer:
outputs, as the notification information, an alert requiring rushing action by the observer in case of emergency.

19. An analysis method according to claim 18, further comprising:
by a server apparatus, receiving the detailed information;
by the server apparatus, storing the detailed information received in the receiving;
information processing; and
providing, wherein
the detailed information includes at least information indicating an excretion date and time, a kind of excrement, and a shape of defecation,
the information processing includes, by the server apparatus, aggregating the detailed information for each shape of the defecation, and
the providing includes, by the server apparatus, providing a processing result in the information processing to an external apparatus.

20. The analysis method according to claim 18,
wherein the alert requires immediate action by the observer to remove the object.

21. A non-transitory computer-readable medium storing a program for causing a computer for control included in an excrement analysis apparatus to perform:
inputting imaging data captured by an image capture apparatus installed in such a way as to include, in a capturing range, an excretion range of excrement in a toilet bowl of a toilet;
first analyzing first analysis target data being imaging data input in the inputting as a real time analysis, and outputting notification information to an observer who observes a user of the toilet;

temporarily holding imaging data input in the inputting; and second analyzing second analysis target data being imaging data that is temporarily held in the temporarily holding as a non-real time analysis, and outputting detailed information indicating a content of excretion, wherein the first analyzer performs an analysis to determine whether a foreign body is present in the first analysis target data, the foreign body being an object other than feces and urine and a subject except for the toilet bowl and washing liquid for the toilet bowl; and in response to determining that the foreign body is present, the first analyzer:

outputs, as the notification information, an alert requiring rushing action by the observer in case of emergency.

22. The non-transitory computer-readable medium storing the program according to claim 21, wherein the program is a program for causing the computer to perform:

receiving, as the detailed information, detailed information including at least information indicating an excretion date and time, a kind of excrement, and a shape of defecation;

storing the detailed information received in the receiving;

information processing to aggregate the detailed information for each shape of the defecation; and providing a processing result in the information processing to an external apparatus.

23. The non-transitory computer-readable medium storing the program according to claim 21, wherein the alert requires immediate action by the observer to remove the object.

*     *     *     *     *